United States Patent [19]
Siciliano et al.

[11] Patent Number: 5,538,869
[45] Date of Patent: Jul. 23, 1996

[54] IN-SITU HYBRIDIZATION PROBES FOR IDENTIFICATION AND BANDING OF SPECIFIC HUMAN CHROMOSOMES AND REGIONS

[75] Inventors: Michael J. Siciliano, Houston, Tex.; Pu Liu, Ann Arbor, Mich.

[73] Assignee: Board of Regents, The University of Texas System, Austin, Tex.

[21] Appl. No.: 70,517

[22] Filed: Jun. 1, 1993

Related U.S. Application Data

[63] Continuation-in-part of Ser. No. 627,945, Dec. 13, 1990, abandoned.
[51] Int. Cl.$^6$ .............................. C12P 19/34; C12Q 1/68; C07H 21/04
[52] U.S. Cl. ........................... 435/91.2; 435/6; 536/24.3; 536/24.31
[58] Field of Search .................. 435/91.2, 6; 536/24.31, 536/24.3

[56] References Cited

U.S. PATENT DOCUMENTS 4,683,195  7/1987  Mullis et al. ............................... 435/6

FOREIGN PATENT DOCUMENTS

| | | |
|---|---|---|
| 0430402A2 | 6/1991 | European Pat. Off. . |
| WO90/01547 | 2/1990 | WIPO . |
| WO90/02821 | 3/1990 | WIPO . |
| WO90/05789 | 5/1990 | WIPO . |

OTHER PUBLICATIONS

Jones and Winistorfer, 1992. "Sequence specific generation of a DNA panhandle permits PCR amplification of unknown flanking DNA," *Nucleic Acids Research*, 20(3):595–600.

Ledbetter et al., (1990). "Rapid Isolation of DNA Probes within Specific Chromosome Regions by Interspersed Repetitive Sequence Polymerase Chain Reaction," *Genomics*, V. 6:475–481.

Ochman et al., 1988. "Genetic Applications of an Inverse Polymerase Chain Reaction," *Genetics*, 120:621–623.

Sugimoto and Himeno, 1991. "A Rapid Isolation of the Unknown 5'–Flanking Sequence of Human CENP-B cDNA with Polymerase Chain Reactions," *Agric. Biol. Chem.*, 55(11):2687–2692.

Trigira et al., 1988. "A procedure for in vitro amplification of DNA segments that lie outside the boundaries of known sequences," *Nucleic Acids Research*, 16(16):8186.

Dionne et al., 1990. "Chromosome Assignment by Polymerase Chain Reaction Techniques: Assignment of the Oncogene FGF-5 to Human Chromosome 4," *BioTechniques*, 8(2):190–194.

Iggo et al., 1989. "Chromosome mapping of the human gene encoding the 68–kDa nuclear antigen (p68) by using the polymerase chain reaction," *Proc. Natl. Acad. Sci. USA*, 86:6211–6214.

Nelson et al., 1989. "Alu polymerase chain reaction: A method for rapid isolation of human–specific sequences from complex DNA sources," *Proc. Natl. Acad. Sci. USA*, 86:6686–6690.

Lichter et al., 1988. "Delineation of individual human chromosomes in metaphase and interphase cells by in situ suppression hybridization using recombinant DNA libraries," *Hum. Genet.*, 80:224–234.

Hochgeschwender et al., 1989. "Construction and screening of a genomic library specific for mouse chromosome 16," *Proc. Natl. Acad. Sci. USA*, 86:8482–8486.

Kariya et al., 1987. "Revision of consensus sequence of human Alu repeats—a review," *Gene*, 53:1–10.

Tkachuk et al., 1990. "Detection of bcr–abl Fusion in Chronic Myelogeneous Leukemia by in Situ Hybridization," *Science*, 250:559–566.

Trent et al., 1989. "Report of the committee on structural chromosome changes in neoplasia," *Cytogenet. Cell Genet.*, 51:533–562.

Harper et al., 1989. "Report of the committee on clinical disorders and chromosomal deletion syndromes," *Cytogenet. Cell Genet.*, 51:563–611.

Rowley, Janet D., 1973. "A New Consistent Chromosomal Abnormality in Chronic Myelogenous Leukaemia identified by Quinacrine Fluorescence and Giemsa Staining," *Nature*, 243:290–293.

de Klein et al., 1982. "A cellular oncogene is translocated to the Philadelphia chromosome in chronic myelogenous leukemia," *Nature*, 300:765–767.

Heisterkamp et al., 1983. "Localization of the c–abl oncogene adjacent to a translocation break point in chronic myelocytic leukaemia," *Nature*, 306:239–242.

Seabright, M., 1971. "A rapid banding technique for human chromosome," *Lancet.*, 2:971–972.

Sumner et al., 1971. "New technique for distinguishing between human chromosomes," *Nat. New Biol.*, 232:31–72.

Pinkel et al., 1988. "Fluorescence in–situ hybridization with human chromosome–specific libraries: detection of trisomy and translocations of chromosome 4," *Proc. Natl. Acad. Sci. USA*, 85:9138–9142.

Lichter et al., 1988. "Rapid detection of human chromosome 21 aberrations by in–situ hybridization," *Proc. Natl. Acad. Sci. USA*, 85:9664–9668.

(List continued on next page.)

*Primary Examiner*—Mindy Fleisher
*Assistant Examiner*—James Ketter
*Attorney, Agent, or Firm*—Arnold, White & Durkee

[57] ABSTRACT

The invention relates to novel primer sets useful in preparing DNA probes specific for any chromosome or part of a chromosome, particularly human chromosomes. The DNA probes so produced may be used to paint individual chromosomes or portions of chromosomes in metephase cell spreads and in interphase nuclei. When used to paint chromosomes in metephase spreads, R-bands are readily detectable. The method is sensitive and has been shown to paint R-bands on chromosomes pieces having as few as several hundred kilobases.

30 Claims, 8 Drawing Sheets

OTHER PUBLICATIONS

Pinkel et al., 1986. "Cytogenetic analysis using quantitative, high sensitivity, fluorescence hybridization," *Proc. Natl. Acad. Sci. USA*, 83:2934–2938.

Zhao et al., 1990. "Detection of t(9;22) in chromonic myelogenous leukemia by fluorescence in-situ hybridization with chromosome-specific composite probes," *Am. J. Hum. Genet.*, 47:A119.

Kuo et al., 1990. "Clinical cytogenetic diagnosis with chromosome-specific DNA probes," *Am. J. Hum. Genet.*, 47:A119.

Le Beau et al., 1983. "Associations of an inversion of chromosome 16 with abnormal marrow eosinophils in acute myelomonocytic leukemia," *N. Engl. J. Med.*, 309:630–636.

Jelinek et al., 1980. "Ubiquitous interspersed repeated sequences in mammalian genomes," *Proc. Natl. Acad. Sci. USA*, 77:1398–1402.

Breukel et al., 1990. "Vector-Alu PCR: a rapid step in mapping cosmids and YACs," *NAR*, 18:3097.

Brooks-Wilson et al., 1990. "Rapid cloning and characterization of new chromosome 10 DNA markers by Alu element-mediated PCR," *Genomics*.

Cotter et al., 1990. "Rapid isolation of human chromosome-specific DNA probes from a somatic cell hybrid," *Genomics*, 7:257–263.

Glover et al., 1990. "Construction of irradiation-reduced hybrids for human chromosome 3 and characterization by IRS–PCR (interspersed repetitive sequence PCR) analysis," *Am. J. Hum. Genet.*, 47:A91.

Kievits et al., 1990. "Direct nonradioactive in-situ hybridization of somatic cell hybrid DNA to human lymphocyte chromosomes," *Cytometry*, 11:105–109.

Dauwerse et al., 1990. "Rapid detection of chromosome 16 inversion in acute nonlymphocytic leukemia, subtype M4: regional localization of the breakpoint in 16p," *Cytogenet. Cell Genet.*, 53:126–128.

Meyne and Moyzis, 1989. "Human chromosome-specific repetitive DNA probes: Targeting in-situ hybridization to chromosome 17 with a 42-base-pair alphoid DNA oligomer." *Genomics*, 4:472–478.

Deininger and Schmid, 1979. "A study of the evolution of repeated DNA sequences in primates and the existence of a new class of repetitive sequences in primates," *J. Mol. Biol.*, 127:437–460.

Singer, 1982. "Highly repeated sequences in mammalian genomes (review)," *Intl. Rev. Cytol.*, 76:67–112.

Manuelidis and Ward, 1984. "Chromosomal and nuclear distribution of the Hind III 1.9-kb human DNA repeat segment," *Chromosoma*, 91:28–38.

Burke et al., 1987. "Cloning of large segments of exogenous DNA into yeast by means of artificial chromosome vectors," *Science*, 236:806–812.

Ludecke et al., 1989. "Cloning defined regions of the human genome by microdissection of banded chromosomes and enzymatic amplification," *Nature*, 338:348–340.

Denninger et al., 1981. "Base sequence studies of 300 nucleotide renatured repeated human DNA clones," *J. Mol. Bio.*, 151:17–33.

Goldberg et al., 1979. "Isolation of specific RNAs using DNA covalently linked to diazobenzyloxymethyl cellulose or paper," *Methods in Enzymology*, 68:206–220.

Noyes and Stark, 1975. "Nucleic acid hybridization using DNA covalently coupled to cellulose," *Cell*, 5:301–310.

Brison et al., 1982. "General method for cloning amplified DNA by differential screening with genomic probes," *Mol. Cell Biol.*, 2:578–587.

Blin and Stafford, 1976. "A general method for isolation of high molecular weight DNA from eukaryotes," *Nuc. Acid Res.*, 3:2303–2308.

van Ommen and Verkerk, 1986. "Human Genetic Diseases, A Practical Approach," ed. by K. E. Davies, 1986, IRL Press, Oxford, England.

Johnson, and de Aroujo, 1981. "A simple method of reducing the faking of immunofluorescence during microscopy," *J. Immunol. Methods*, 43:349–350.

Thompson et al., 1989. "Complementation of repair gene mutations on the hemizygous chromosome 9 in CHO: a third repair gene on human chromosome 19," *Genomics*, 5:670–679.

Liu et al., 1989. "Human DNA excision repair gene ERCC4 is located on chromosome 16 short arm 16p13.13–p13.3," *Cytogenet, Cell Genet.*, 51:1035.

Liu et al., 1989. "Isolation of human transcribed sequences from human-rodent somatic cell hybrids," *Science*, 246:813–815.

Stallings et al., 1988. "Human creatine kinase genes on chromosomes 15 and 19, and proximity of the gene for muscle form to the genes for apolipoprotein C2 and excision repair," *Am. J. Hum. Genet.*, 43:144–151.

Thompson et al., 1985. "Correction of a nucleotide-excision-repair mutation by human chromosome 19 in hamster-human hybrid cells," *Somat. Cell Molec. Genet.*, 11:87–92.

Lichter et al., "Fluorescent in situ Hybridization with Alu and L1 Polymerase Chain Reaction Probes for Rapid characterization of Human Chromosomes in Hybrid Cell Lines," *Proceedings of the National Academy of Sciences USA*, 87:6634–6638, 1990.

Lengauer et al., "Painting of Human Chromosomes with Probes Generated from Hybrid Cell Lines by PCR and Alu and L1 Primers," *Human Genetics*, 86:1–6, 1990.

International Search Report, mailed Apr. 29, 1992.

Henske, Elizabeth P. et al., "A Radiation–Reduced Hybrid Cell Line Contaiing 5 Mb/17 cM of Human DNA from 9q34," *Genomics*, 13:841–844, 1992.

Liu, Pu et al., "Dual Alu Polymerase Chain Reaction Primers and Conditions for Isolation of Human Chromosome Painting Probes from Hybrid Cells," *Cancer Genet. Cytogenet.*, 65:93–99, 1993.

Rowley, Janet D. et al., "Mapping Chromosome Band 11q23 in Human Acute Leukemia with Biotinylated Probes: Identification of 11q23 Translocation Breakpoints with a Yeast Artificial Chromosome," *Proc. Natl. Acad. Sci. USA*, 87:9358–9362, 1990.

Ziemin-Van Der Poel, Sheryl et al., "Identification of a Gene, *MLL*, That Spans the Breakpoint in 11q23 Translocations Associated with Human Leukemias," *Proc. Natl. Acad. Sci. USA*, 88:10735–10739, 1991.

IN-SITU HYBRIDIZATION PROBES FOR IDENTIFICATION AND BANDING OF SPECIFIC HUMAN CHROMOSOMES AND REGIONS

The United States Government may have certain limited rights in the present invention pursuant to the terms of Grant No. CA34936 and Grant No. CA04484 awarded by the National Institutes of Health.

This is a continuation-in-part of U.S. patent application Ser. No. 627,945 filed on Dec. 13, 1990, now abandoned, the entire text of which is herein incorporated by reference and without disclaimer.

BACKGROUND

1. Field of the Invention

The invention relates generally to the preparation of chromosome specific DNA probes that are useful in selectively detecting individual chromosomes or chromosome segments. The method may be used for detection of chromosomes or chromosome segments in metaphase cell spreads and in interphase nuclei by in-situ hybridization.

2. Description of Related Art

Chromosome identification procedures have long been considered an integral aspect of biomedical diagnostic practice because of the many disease syndromes having a genetic basis which are caused or diagnosed by chromosomal alterations. Being able to observe these chromosomal alterations in cells of the body, therefore, not only helps in the diagnosis of the disease but has the potential of being an effective monitor of therapeutic procedures designed to eliminate the cells with the chromosomal anomalies from the body. It is also important to be able to rapidly monitor the chromosomes of the fetuses of pregnancies at risk (such as in older women, or where a parent may have been exposed to environmental mutagen, or where previous siblings of the fetus have an abnormality with known chromosomal basis). Specific chromosomal abnormalities, translocations (exchanges between the arms of two different chromosomes), inversions (internal segment of a chromosome swings around and faces the opposite direction), deletions (piece of chromosome becomes lost), monosomies (only one instead of two chromosomes of a type), and trisomies (three instead of two chromosomes of a type) have been associated with specific sub-types of cancer (1) as well as in a wide variety of inherited or congenital abnormalities (2).

Chromosomally based disease syndromes are often seen in hematological malignancies such as leukemia and lymphoma. The classic example is the 9:22 translocation associated with chronic myelogenous leukemia (CML). Here, there is a reciprocal translocation between the end of the long arm of chromosome 9 and the middle of the long arm of chromosome 22 producing what is known as the Philadelphia (Ph) chromosome of the translocation chromosome carrying the chromosome 22 centromere (3–5). The ability to see such events was made possible by a staining method developed in the early '70s which imparted to each of the 24 different human chromosomes a distinctive banding pattern (6,7). Therefore, by carrying out such a stain on cells and photographing them, individual chromosomes can be cut out and lined up (according to their bands) in a procedure called karyotyping. By doing this the translocation, or any abnormal chromosome eventually stands out from the rest and is identified.

While effective and important in original diagnosis, this procedure is impractical for determining the percentage of such cancer cells in patients with minimal residual disease or in relapse because it is arduous and labor-intensive. Furthermore, with respect to monitoring pregnancies, a faster method is preferred. A disadvantage of the procedure is its dependence on high quality metaphase spreads (structures formed when the chromosomes condense and form their distinctive morphology and banding pattern during the division phase of the cell cycle). Good, scorable metaphases are often not available in the tissues which one needs to monitor (e.g., bone marrow which is the source of many leukemic cells, or amniocentesis tissues for fetus evaluation). The result is that rearranged chromosomes are often not identifiable by this method leaving the entities of unknown origin to be referred to as "marker chromosomes".

Two groups (8,9) have described a method to stain a specific chromosome of choice. The problem associated with such a procedure was to obtain DNA from only the chromosome of interest, label it in some way so that it would be identified later (this labeled DNA is therefore chromosome-specific "probe"), and then hybridize probe to the chromosomes in a cell on a microscope slide. By visualizing the label, the chromosome was visualized since the DNA, if properly handled, hybridized only to the chromosome from which it was derived. The procedure has since come to be known as chromosome painting. Using a human chromosome 21 probe, trisomies and translocations associated with the chromosome (9,10) were visualized even in poorly defined metaphases. Specific chromosomes of interest used to prepare painting probes have been separated from other chromosomes by flow-sorting synchronized populations of dividing cells through a technically rigorous procedure requiring highly specialized and expensive equipment (a fluorescence-activated cell sorter). This leads to only a small quantity of material, so that the DNAs from the individual chromosomes then need to be extracted and cloned into cosmid libraries. To make probe, the cosmid library must be expanded, DNA extracted again and nick-translated in the presence of biotinylated nucleotide prior to hybridization to human metaphase spreads and detection of the specific chromosomes (11). An essential requirement for specific chromosome painting is the prehybridization of the probe with total human DNA in order to prevent human repeat sequences (which are not chromosome specific) from participating in the in-situ hybridization reaction.

Unfortunately, flow sorting of individual chromosomes, making and expanding and maintaining cosmid libraries is problematical because of possible contamination with other chromosomes or the presence of non-chromosomal specific sequences in such material that cannot be prevented from participating in the in-situ hybridization. These concerns have been recently highlighted (12) in studies where such probe made for human chromosome 22 hybridized to additional chromosomal regions on human metaphases. Other serious limitations of the approach include: 1) cross-hybridization of the chromosome 2 probe to the centromere of chromosome 19; 2) failure of libraries made from chromosome 5 to paint chromosome 5; 3) cross-hybridization of probes made from flow-sorted chromosomes 13, 14, 15, 21, and 22 to the centromeric regions of each other; and 4) cross-hybridization of the chromosome 18 probe to the centromeric regions of chromosomes 12 and 19 (as in poster presentation at the 41st Annual Meeting of the American society of Human Genetics—13). The method is also expensive and limited to the availability of the flow sorted libraries. The procedure is relatively inflexible. For instance, there are situations in which one might be interested in painting only a portion of a specific chromosome (e.g., the p-arm of chromosome 16). This has not yet been achieved using flow-sorted libraries, yet this would be an excellent probe for the identification of inversions associated with cancer and other disease syndromes. An example of this is acute nonlymphocytic leukemia where there is a pericentric inversion involving both the short and long arms of chromosome 16 (14). Probe for only the short arm of the chromosome would identify the inversion chromosome as one which had staining on portions of both arms whereas a normal chromosome 16 would have only the short arm painted. Finally, probe made from flow sorted chromosome libraries does not allow the identification of the regions of the respective chromosomes brought together by the rearrangement because the longitudinal differentiation (banding) of the specific chromosome is lost and probes to paint specific portions of chromosomes are not available by this method. Therefore, the approach is not effective in identifying either break point sites in rearrangements or deletions (or other events in which only a single chromosome is affected).

Another way to isolate human chromosome-specific DNA is amplification by polymerase chain reaction (PCR) from interspecific hybrid cells containing only the human chromosome or chromosomal region of interest. Human-rodent hybrid cells monochromosomal for virtually every human chromosome and for portions of a human chromosome are now available. Since it is known (15) that the human genome has hundreds of thousands species-specific repeat sequences scattered throughout, several groups (16–19) have prepared consensus primers to bind to these sequences. By using these primers for PCR amplification, some success in pulling out human chromosome specific DNA sequences from hybrid cells and various types of recombinant DNA libraries have been achieved. However, a recently reported attempt to make painting probe from such material (20) resulted in speckled chromosomes with high background with no possibility of observing any longitudinal differentiation of the painted genetic element. Although selective in amplifying human DNA from hybrid cells, sensitivity in chromosome painting was low. Thus, the reported methods are impractical for developing probe useful for the identification of deletions or translocation breakpoints in abnormal cells.

An attempt to paint specific human chromosomes with the total DNA from a hybrid cell containing the human chromosome of interest has met with partial success (21). Unfortunately, for most of the chromosomes attempted, no clear specific painting was obtained. In the few cases where success in painting a specific chromosome was achieved, the entire chromosome was painted and there was no possibility of observing longitudinal differentiation.

Identification of cells having chromosomal rearrangements at known breakpoints on the affected chromosomes has been accomplished by using, as probe, sets of cosmids that flank the breakpoint. Use of such cosmid probes flanking the breakpoint region of the p-arm of chromosome 16 has enabled visualization of the inversion associated with acute nonlymphocytic leukemia (22). However, the intensity of the signal was relatively weak. One would expect a much stronger signal if the entire arm of the chromosome were painted. Using a similar technique, the CML Ph chromosome has been identified using a pair of cosmids, one from the brc gene proximal to the breakpoint on chromosome 22 and the other from the abl gene distal to the breakpoint on chromosome 9 (23). The intensity of the signal appeared weak, raising doubt that it could be reliably used to identify the breakpoint in the majority of cells without computer enhancement. These latter two approaches, while somewhat effective for chromosomal alterations where genomic regions flanking the breakpoints have been cloned, are useful only where such sites have been precisely identified or isolated. In the vast majority of cases, the sites are unknown and there is no effective method of identification.

Finally, DNA probes have been developed that specifically detect the centromeres (the dot-like structure at the junction of the two chromosome arms) for particular chromosomes (24). These probes are supposed to be effective in determining the number of chromosomes (for chromosomes from which such probes have been developed) in cells (24). However they provide no information on rearrangements involving those chromosome. Additionally, they often lack specificity in that probe developed for the identification of one centromere will often cross-hybridize to centromeres of other chromosomes.

Some progress has been made in developing techniques to selectively identify individual human chromosomes. However, current methods have several shortcomings, including: (1) lack of detection of abnormal chromosomes in less than ideal metaphase spreads; (2) impracticality in determining the frequency of abnormal cells in a complex tissue; (3) inefficient detection of identify of marker chromosomes; (4) lack of specificity in identifying sub-chromosomal regions; (5) great time and expense involved in either karyotyping or preparing probe; (6) lack of flexibility; and (7) failure to paint chromosomes adequately while still observing landmarks for longitudinal differentiation.

SUMMARY OF THE INVENTION

The present invention seeks to overcome these and other drawbacks inherent in the prior art by providing a highly efficient and selective means for identifying individual chromosome abnormalities, as well as marker chromosomes in interphase and as metaphase nuclei. The disclosed methods have the flexibility to develop probe for specific chromosomal regions and permit the efficient manufacture of probes that will not only brightly paint a human chromosome of interest, but will also paint a banding pattern on the chromosome to enable the identification of the sites of chromosomal aberrations.

The inventors have devised methods of preparing DNA probes that are specific for virtually any desired chromosome or sequences. The probes obtained by this method are significantly greater in number than typically produced by amplification methods. The probes contain only a relatively small amount of species specific repeat sequence. The repeat DNA segments are readily blocked or removed. Probe prepared in this manner hybridizes specifically to the chromosome or chromosome segment from which it was prepared, usually with a distinct banding pattern when labeled for in situ hybridization.

As used herein, the terms "probes" and "probe" are used interchangeably to designate the collection of DNA segments produced by amplification of chromosome specific DNA regions between species specific repeat segments. The numerous DNA segments act as a "probe" for the specific chromosome or chromosome segments from which they are obtained.

In general, chromosome specific DNA probe may be prepared by first isolating the desired DNA and then amplifying only regions of chromosome specific DNA. This is achieved by hybridizing primers to certain regions of a species-specific repeat sequence, then amplifying. The DNA between the repeat segments is amplified, but little if any of the repeat segment is synthesized. The resulting DNA probe is to a great extent free of species specific repeat DNA sequences to which the primer was hybridized, generally lacking, for example, about ⅔ of Alu repeat segments.

In the practice of the invention, one should determine or select the particular a chromosome or part to which probes are desired. The chromosome may be selected from any number of sources, including insects, birds, fish, humans, animals or any living thing that has a chromosome with chromosome-specific DNA sequences and a sufficient number of interspersed segments with species specific repeat DNA sequences. Mammals, including humans, have such interspersed segments, for example, LINES or SINES. Clustered repeat sequences are also found in some species, for example the alphoids found in humans. One type of SINE found in mammalian species is the Alu repeat sequence. The chromosome, or portion thereof, need not be free of chromosomes from other species as long as its species specific segments are different enough in sequence from the repeat segments of the other species so that primers for polymerase chain reaction (PCR) may be prepared which will selectively bind to the sequences of the repeat segments associated with desired species.

DNA for preparing probe may be obtained from any source in which the chromosome, or segment thereof, has been isolated from the remainder of that species other chromosomal material. These sources include interspecific somatic cell hybrids, flow-sorted preparations, microbial vector clones, or microdissected DNA. In a most preferred embodiment the chromosome or portion thereof to which probe is being prepared is isolated in interspecific somatic cell hybrids, such as hamster.

In the practice of the invention, one prepares at least two primers for use in subsequent PCR amplification, each primer hybridizing to a region within the same repeat segment. The first primer or primers will preferably bind at or near the 5' terminus of such a repeat segment within the chromosome or chromosome segment. The primer facilitates DNA replication in the direction of the repeat DNA segment 5' terminus. Similarly, one or more primers of the second group of primers will preferably bind at or near the 3' terminus of a repeat segment and will facilitate DNA replication in the direction of the 3' terminus.

After the primers are prepared, an annealing step is performed by hybridizing with DNA obtained from the material containing the chromosomal region of interest. Annealing by hybridization techniques is well known to those skilled in the art and generally is conducted at a temperature between about 50° C. and 60° C. In one aspect of the present invention, when interspecific somatic cell hybrids are the source of the chromosomal material for which probe is being made, hybridization is performed at a higher temperature, in the range of 60°–70° C., most preferably at 65° C. This prevents annealing of the primers to repeat segments in chromosomes of the other species.

A final step in preparing chromosome specific DNA probes is amplification of the inter-repeat regions of the selected chromosome or chromosome segment. For human chromosomes, the DNA amplified will be specific for that particular chromosome or chromosome segment. Since DNA synthesis is directed away from the middle and off the termini of each human Alu repeat segment, the DNA probe so produced will contain a minimum amount of Alu repeat sequences. A small amount of Alu repeat sequence amplified will arise because the primer sets do not bind to the very ends of the Alu repeat segments.

In humans as well as other mammals, species specific repeat sequences occur frequently. Segments of Alu repeat sequences are the most prevalent middle repeat elements in human chromosomes. When the method is used to prepare human chromosome or human chromosome portion-specific DNA probes, the first primer or primer set (Alu-1) is designed to bind to base pairs 13–31 from the 5' end of a 300 bp Alu segment. In a preferred embodiment, the first primer or primers have a sequence which is reverse complementary to the Alu consensus sequence located from base pair 13–31. This means that priming with Alu-1 will direct DNA synthesis toward the 5' terminus, and away from the middle, of the Alu segment in which the primers bind. In preferred embodiments, complementarity to the consensus sequence is sufficiently degenerate so that binding to a large number of human Alu segments occurs. This is accomplished using a set of primers synthesized so that, in combination, the primers will bind to virtually all Alu segments. In this embodiment, the primers do not bind with Alu segments of nonhuman species.

More preferably, members of the Alu-1 set have the base sequence GGATTACAGGYRTGAGCCA (seq id no:1). Y is either pyrimidine T or G and R is either purine A or G. The Alu-1 primer set most preferably comprises four primers with either thymidine or cytosine at position 11 and adenine or guanidine at position 12. The primers are preferably used in approximately equal amounts. These primers will bind to a large number of human Alu consensus segments but not to nonhuman Alu segments. It will be appreciated by those of skill in the art that other primers may be effective in the practice of the invention, such as somewhat shorter or longer primers. Also, fewer than four primers may be used. The closer the primer binds to the 5' end of an Alu 300 bp repeat segment, the less Alu repeat sequence DNA will be obtained on subsequent amplification of chromosome specific DNA. Although binding at the very end of human Alu sequences would be desirable, Alu sequences are less conserved at that position and a sufficiently consensus sequence is not identified. It is preferred that the primer bind to as many Alu regions as possible in order to promote amplification of as much chromosome specific DNA as possible. It should also be appreciated that repeat segments other than Alus occur in human chromosomes. Analogously designed primer sets could be used with the Alu primers to eliminate essentially all repeat segments.

A second primer set (Alu-2) is also designed to bind with a human Alu consensus sequence, but these primers will preferably bind at or near a 3' terminus of a 300 bp Alu segment, not at the 5' end. The primers in Alu-2 have a base sequence identical to a base sequence within an Alu repeat segment and therefore prime to direct DNA synthesis in a 3' direction, that is, away from the center of the 300 bp Alu segment to which they are annealed. A preferred consensus sequence is located within 100 base pairs of the 3' terminus, most preferably at base pair position 240–258 of 300 bp Alu repeat segment. The primers in Alu-2 most preferably have base pair sequences that bind with the majority of human Alu repeat segments. This is accomplished by taking into account the degeneracy of consensus sequences within Alu segments and preparing a mixture of primers with base sequences which bind with nearly all the consensus sequences. The primers in the Alu-2 set comprise primers having the base sequence RCCAYTGCACTCCAGCCTC (seq id no:2) where R is A or G and Y is T or C. The Alu-2 primer set has four primers, preferably used in approximately equal amounts.

In a particular aspect of the invention, human chromosomes or segments of chromosomes are used to prepare specific probe. For example, any of the 24 different human chromosomes (number 1–22, the X and the Y) may be isolated in various hybrid cells and used to prepare probe specific to that chromosome by the disclosed method. Additionally, a segment of a chromosome may be used, for example, the p-arm of chromosome 16, band q13.3 of chromosome 19, 1q, 3q, 5q, 7q, 9q or 22q. The method has been demonstrated with portions of a chromosome as small as 1–2 Mb of human DNA from band q13.3 of human chromosome 19. The lower limit of detection may be as low as 500 base pairs in situations where specific DNA bracketed by repeat sequence is obtained and amplified as probe by the method described.

DNA of the desired chromosome may be isolated from species total chromosomal material by flow sorting or, preferably when shorter segments of the chromosome are desired, from interspecific somatic cell hybrids, artificial yeast chromosomes, or radiation hybrids. Isolation may also be by microdissection of the desired DNA.

The invention also relates to a method for painting a human chromosome or portion of a human chromosome in metaphase spreads or interphase nuclei. One removes the remaining segments of repeat segments as described herein. The probes are then labeled with a substance that can be later detected, for example, biotin, digoxigenin, $^{32}P$, dinitrophenol, aminoacetylfluorene or conjugated mercury, and incubated with a sample in which the human chromosome or portion is to be identified by in-situ hybridization, conjugated, for example, with avidin-fluorescein, Texas red, fluorescein isothiocyanate or acid phosphatase and detected by one of a series of methods such as fluorescence, autoradiography or chemoluminescence. These are procedures well known to those skilled in the art. Biotin is the preferred label, avidin-fluorescene the preferred conjugant, and fluorescence the preferred detection method.

Small amounts of amplified repeat sequences amplified from the human chromosome of interest and which are not chromosome specific may be prevented from participating in the in-situ hybridization reaction. This may be accomplished by blocking those non-chromosome-specific regions with middle- and highly-repetitive DNA isolated from the total DNA of the species, most preferably Cot 10 DNA.

The invention also includes a method of removing small amounts of amplified repeat sequence DNA from the in-situ hybridization probe using PCR amplified Alu repeat sequence terminal regions. Plasmid comprising a complete 300 bp species specific repeat Alu sequence is used, preferably Blur2. Two primers are then prepared that will anneal each of the two plasmid arms. These primers, and Alu-1 or Alu-2 primers are annealed to DNA from the plasmid. PCR is conducted in order to amplify the repeat sequences from the two ends of the Alu segment (bp 1-bp 31 and bp 240-bp 300). The amplified Alu terminal regions are linked to a carrier, then the labeled Alu sequences from the probe DNA are hybridized to them. This removes the terminal Alu repeat sequences from the probe to be in-situ hybridized. A preferred carrier useful for linking with amplified Alu terminal regions is diazobenzoxymethyl cellulose although other carriers such as diazotized plastic beads may also be used. Where repeat sequences are prevented from participating in the in-situ hybridization reaction by blocking, the efficiency of that blocking reaction can be increased by the addition of the amplified Alu terminal regions to the middle and highly repetitive DNA used for such purpose.

The chromosome painting method may also be applied to painting of R-banding patterns on specific human chromosomes in metaphase spreads. Good metaphase spreads are not critical.

The present invention also contemplates the use of human Alu primer sets and specific chromosome probes in kit form. Thus in a preferred mode of use, lyophilized human specific inter-Alu-1 and inter-Alu-2 primers will be employed to conveniently amplify a selected human chromosome or portion of human chromosomes to produce DNA probe directed to that particular DNA. In yet another preferred mode of use, labeled DNA probe specific for selected human chromosomes is provided as probe. This may include DNA probes for human chromosomes 1–22 and the x and y chromosome as well as chromosome segments such as 16p, 19 q13.3, 9q, 9q34, 5q, 7q, 3q, 1q and the like.

The invention also includes two unique primer sets each comprising four primers especially designed for use in the production of human specific probe for any desired chromosome or part thereof. Each set may comprise one or more primers but is most preferably four primers. The base sequence of one primer set is GGATTACAGGYRTGAGCCA (seq id no:1) and the base sequence of the second primer set is RCCAYTGCACTCCAGCCTG (seq id no:2) where Y represents T or C and R is A or G. There are four primers in each set and in a preferred mode of use are used as mixtures of approximately equal amounts.

BRIEF DESCRIPTION OF THE DRAWINGS

FIG. 1A shows PCR conducted under standard conditions, annealing temperature 55° C. FIG. 1B shows the PCR annealing temperature at 65° C.

FIG. 20A shows a human Alu repeat sequence with the 5' and 3' conserved regions indicated in bold face from base pairs 13–29 and 240–258, respectively. Primer Alu-1 is constructed as the reverse complementary sequence of the 5' conserved region so that after denaturation it will anneal and, in the presence of Taq polymerase, replicate off the 5' end of the segment. Primer Alu-1 is a direct complementary sequence and as such will prime off the 3' end of the segment during PCR reaction. GGCTGGGCGTGGTGGCTCAYRCCTGTAATCC is seq id no:3; CCGACCCGCACCACCGAGTRYGGACATT-AGG is seq id no:4; RCCAYTGCACTCCAGCCTG is seq id no:2; and YGGTRACGTGAGGTCGGAC is seq id no:5. FIG. 20B illustrates the consequences of the primer design and using primers simultaneously in a PCR reaction on human genomic DNA. Inter-Alu sequences are amplified irrespective of the orientation of the Alu sequences in the template genomic DNA.

FIG. 21B and FIG. 21D show the appearance of the labels when viewed under a fluorescence microscope.

DETAILED DESCRIPTION OF THE PREFERRED EMBODIMENTS

Figure 1A:
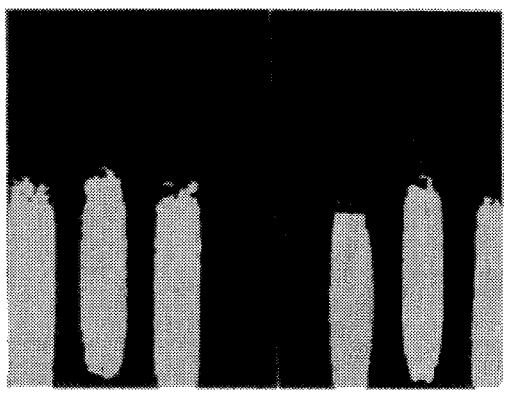
FIGS. 1A and 1B show the agarose gel separation of inter-Alu-PCR products using both Alu-1 and Alu-2 primers (½), Alu-1 primer only (1), or Alu-2 primer only (2) on HeLa DNA and CHO DNA. Unmarked channels are size markers.

The invention relates generally to the preparation of human chromosome specific probes that are either blocked for or obtained free of the major portion of non-chromosome specific repeat sequences. Such probes when applied to human cells via the process of in-situ hybridization, will identify the human chromosomal region of interest. The procedure allows the rapid identification of chromosomal abnormalities associated with various forms of cancer and birth defects.

A novel aspect of the invention is the design, preparation and conditions for use of two sets of consensus Alu-PCR primers for manufacture of the chromosome specific probes by inter-Alu-PCR. The scheme takes advantage of the fact that Alu segments are distributed throughout the human genome and that by using them to instigate PCR reactions, unique, chromosome-specific sequences located between such segments may be amplified for use as probe for chromosome identification. Alu sequences are of the most abundant family of middle repetitive DNA sequences in the human genome. About 500,000 Alu family members are present in the haploid human genome, amounting to about 6% of the total mass of the DNA (25). These Alu sequences are not precise copies of a single sequence but instead are related copies of a consensus sequence which is approximately 300 base pairs (bps) long and consists of two monomer units.

Alu primers were designed based on several considerations. First, it was necessary to insure that a maximum number of Alu sequences were annealed by the primers. It is estimated that the average divergency of Alu sequences from the consensus is 12% (26). This divergency (or degeneracy) needs to be considered in the design of the primers in order for them to anneal with as many Alu sequences as possible. Second, since the Alu sequences themselves are not chromosome specific, it was necessary to insure minimum representation of the Alu sequence themselves in the product of the inter-Alu-PCR without impairing the first consideration. Therefore, the primers had to be designed to recognize the ends of Alu segments and direct priming away from the middle of such segments. Third, the primers needed to be designed so that inter-Alu-PCR would occur independent of the orientation of Alu segments in the human DNA to maximize the amount of unique sequence amplification. Finally, the primers needed to be human specific in order to amplify selectively human DNA in the presence of excess DNA from other species.

The Alu primers were designed based on a current revision of consensus sequence of human Alu repeats (25). The revision was based on nucleotide sequences of 50 different, cloned and sequenced human Alu segments. Two regions on the sequence showing high degree of conservation among Alu family members were identified. One is at bp 10–50 and the other at bp 240–260. These were the candidate regions for the primer locations. One provided the basis for design of the first primer (Alu-1) that bound near the 5' end of a 300 base pair (bp) Alu segment, and a second stretch was used to design the second primer (Alu-2) which bound near the 3' end.

In considering the first or 5' region, it was noticed that there was a lack of sequence conservation around position 20. At position 20, 31% of the segments had a T rather than C; and at position 21, 42.5% of the Alu sequences had an A instead of G. In order to maximize binding of primers at this region, degeneracy at these two positions was taken into consideration in primer design. Bp 10–12 could not be used because there were substitutions of more than one nucleotide at those positions. Therefore, the Alu sequence selected for the design of the Alu-1 primer went from bp 13 to bp 31 and, taking degeneracy into consideration, had the sequence TGGCTCA(C/T)(G/A)CCTGTAATCC (residues 13 to 31 of seq id no:31). In order to minimize the incorporation of Alu sequence itself in the product of the inter-Alu-PCR, the primer was designed to recognize that region and to direct DNA synthesis off the 5' end and away from the middle of the Alu segments to which it bound. Therefore, the actual Alu-1 primer is the reverse complement of that sequence or GGATTACAGGYRTGAGCCA (seq id no:1) (where Y is either pyrimidine, C or T; and R is either purine, A or G).

For the second or 3' region there were regions of degeneracy at bp positions 240 and 244. At bp 240, 37.5% of the Alu members had an A instead of G. At position 244, 32.7% had a T instead of a C. For the same reason as above, degeneracy was incorporated into the primer design and the sequence of primer Alu-2 is RCCAYTGCACTCCAGC-CTG. This is a direct and not an inverse complementary sequence directing priming off the 3' end of an segment.

Since each primer reads away from the middle of the Alu segment, the resultant inter-Alu-PCR will not only be initiated from a maximum number of Alu segments but also incorporate a minimum amount of Alu sequence. Furthermore, the design takes into consideration the fact that two adjacent Alu sequences could be arranged head to head, tail to tail or in tandem. Having one primer at each end with the direction of DNA synthesis away from the Alu segment enables amplification between any two Alu sequences independent of their orientation when the two Alus are within appropriate distance for PCR. This yields product ranging from a few hundred to several thousand base pairs. Therefore, the primer design maximizes both the number of Alu segments recruited and the number of inter-Alu unique sequences amplified while minimizing the amount of Alu sequence incorporated into the reaction products and defines the DNA probes as practiced by this invention.

Comparing Alu-1 and Alu-2 with rodent Alu-like consensus sequences (27) indicated that 11 nucleotides at the 5' end of Alu-2 are not present in either Chinese hamster or mouse. For Alu-1, there are 7 mismatches in Chinese hamster sequence and there is no corresponding sequence in mouse. Therefore, it was possible to establish conditions for the specific amplification of human DNA using these two primers in the presence of rodent DNA. Thus, when there is only one, or part of only one, human chromosome in the DNA from a human x rodent cell line subjected to the PCR, the amplified DNA will be specifically from that human chromosomal region. This material can then be used for in-situ hybridization to identify the location of those unique sequences in the human genome.

As a second innovative feature, this method is designed to be used on DNA from interspecific somatic cell hybrids that retain only a single, or part of a single, human chromosomal element isolated against a rodent chromosomal background. By conducting the PCR reaction, under conditions described below, on the DNA from such cells using the primers designed above, only the human DNA (representing the human chromosomal material on interest in the hybrid cell) will be manufactured in large quantity by PCR amplification.

In this procedure, the temperature conditions for the crucial annealing step of PCR are elevated above the standard temperature used for the reaction because variations of the consensus sequences recognized by the primers (Alu-1 and Alu-2) also exist (as indicated above—27) in the rodent versions of Alu segments (Alu sequences have some level of evolutionary conservation in mammalian species). At standard temperatures of annealing, the primers may bind to rodent Alu sequences of shared homology, thus decreasing specificity toward human chromosomal material present in the hybrid cell. However, at higher temperatures, the sequences of the primers and the human Alu sequences to which they are designed to bind, must be more precisely matched allowing the Alu primers designed to recognize consensus human Alu sequences to amplify only the human chromosomal material present in the DNA.

For this amplified DNA from a specific chromosomal region to function effectively as probe to identify that specific chromosomal region in a human cell, repeat sequences present in the DNA must be prevented from taking part in the in-situ hybridization reaction for which the probe material will be used (8,9). This is necessary since, in addition to the chromosomal-specific unique sequences, the inter-Alu-PCR reaction will amplify Alu repeat sequences located at the ends of the Alu segment sites of priming as well as other types of non-chromosomal-specific repeat sequences which might be located between Alu segments participating in the reaction. Since such repeat sequences are not specific for the chromosomal region of interest, in the in-situ hybridization reaction, they will hybridize to chromosomal regions on other human chromosomes. These repeat regions were effectively prevented from participating in the reaction by designing a blocking agent made from total human DNA. This was accomplished with high efficiency isolation of a repeat sequence-rich fraction of human DNA (called low-Cot DNA) and prehybridizing to probe DNA. This effectively blocked the participation of the repeat sequence regions in the in-situ hybridization reaction and gave the probe its specificity to the chromosome region of interest.

Another important unique feature of this approach is that preparing probe in this manner (inter-Alu-PCR) results in probe that not only binds specifically to the human chromosome of interest but will also impart to that human chromosome a banding pattern. This makes it possible to identify regions where the normal chromosome structure has been modified (by deletion, translocation or inversion). The observed banding pattern is resolved because Alu sequences are not homogeneously distributed throughout the human genome but rather are in higher concentration in specific regions (R-bands) along the length of the chromosomes (28). Consequently, probe made by inter-Alu-PCR from a human chromosome DNA will bind preferentially, not only to the human chromosome from which it was derived, but also to the longitudinally-specific regions of that chromosome that are rich in Alus. Therefore, the procedure will not merely paint the human chromosome of interest, but will paint on the chromosome the specific banding pattern unique to it.

Figure 4:
FIG. 4 is a photomicrograph of a human metaphase spread after in-situ hybridization with inter-Alu-PCR probe obtained from the hybrid containing human chromosome 19 as the only human genetic element. Arrows indicate two fluorescing chromosomes, identified as the human 19 chromosomes. Note the absence of fluorescence at the centromeres (tips of the arrows).

Since the centromeric regions of chromosomes are rich in the highly repetitive alphoid repeat sequences (which are a different class of repeat sequence than Alu) (24), they are not amplified by the inter-Alu-PCR. Consequently the centromeric regions of the chromosomes are not painted by probe made by this method (e.g., FIG. 4). Painting probes which include centromeric regions are often not chromosome specific because those non-chromosomal specific regions are not readily blocked (due to the highly repetitive clustered nature of such sequences, as opposed to the middle repetitive status of the interspersed Alu repeats) or eliminated from the in-situ hybridization reaction (12,13). Eliminating such regions in the design of our probes enhances their chromosomal specificity.

One of the special advantages of making in-situ hybridization probe for specific chromosome regions by inter-Alu-PCR from hybrid cells containing only those regions of the human genome is the flexibility provided by being able to prepare probe that identifies only chromosomal arms, regions or sub-regions. Such probe can readily identify chromosomal abnormalities involving only a single chromosome (inversions or deletions) as indicated in Example 8.

In addition chromosome region-specific probes make it possible to identify and resolve those regions in an interphase nucleus (the compartment of the cell cycle in which upwards of 90% of the cells are located). In interphase, the chromosomes are not visible because they are not condensed. It is a well recognized phenomenon that in-situ hybridization probe for a specific chromosome will identify the domain that chromosome occupies in an interphase nucleus (8,9). Since chromosomes are "unwound" in that phase, entire chromosomes present very large, unresolved domains of hybridization. By being able to make probe from only a small fraction of a chromosome, the domain visualized becomes smaller and better resolved. The identification of chromosomes and chromosomal abnormalities in such nuclei then becomes possible. The demonstration of such resolution using such probes and indication of their usefulness in observing intra-chromosomal abnormalities in interphase nuclei is cited in Example 9.

However, the identification of translocations in interphase nuclei by using combinations of two such probes tagged so that they fluoresce in two different colors and which are derived from small regions of the affected chromosomes flanking the translocation breakpoints is a major application of inter-Alu-PCR probes to interphase nuclei. The translocation is observable as a combination of the two colors in those nuclei. Since these chromosome regions, from which probes are made by the invented method, are measured in millions of base pairs in length the signal they give is quite outstanding and observable in every cell nucleus without the need for computer enhancement (as in Example 9). This distinguishes them from current methodology in which human cosmid clones flanking the translocation breakpoint sites are labeled with different color probes and used to observe the translocations in interphase nuclei (23). Since the cosmid clones are only tens of thousands of base pairs in length, the signal is weak and not reliably visualized in every interphase.

This ability to reliably determine if the translocation chromosome is present in interphase nuclei will be of major importance in the management of minimal residual disease during cancer chemotherapy. In such cases one wishes to determine the low frequency of cells in the bone marrow of a leukemia patient that had, or is undergoing, treatment. Since that frequency is low (perhaps $1/1000$ or $1/10,000$) it is impractical to make the determination from only the few cells in metaphase that one recovers from such preparations. It is also likely that the cells in metaphase might be a disproportionate representation of a single cell type and not representative of the population of cells as a whole. The ability to see the translocation in the interphase cell will not only be an excellent monitor for the effectiveness of treatment but also be an extremely useful research tool in determining the etiology of the disease.

While the present methods were designed for preparing in-situ hybridization probe by amplifying human chromosomal regions isolated in hybrid cells, the inter-Alu-PCR method will also be effective in providing probe from chromosome regions isolated by other methods—flow-sorted human chromosomes (8,9); chromosome regions cloned into large insert microbial vectors such as yeast artificial chromosomes (YACs (29)); or chromosome regions scraped by microdissection from a microscope slide (30). In these cases it will not be necessary to increase the annealing temperature for the PCR reaction since there is no danger of amplifying contaminating (non-human) DNA.

While the innovative procedure for blocking repeat sequence DNA from participating in the in-situ hybridization reaction is effective, the present invention also includes a method to completely remove repeat sequences. Therefore, the hybridization reaction may be conducted with pure unique sequence specific to the chromosomal region of interest. As discussed above, there are two sources of repeat sequence in the inter-Alu-PCR probes that require elimination. The first source is present because of the fact that primers Alu-1 and Alu-2 are not located at the very ends of Alu segments (the very ends, although still Alu, are not sufficiently conserved to be able to identify a useful consensus sequence for use as primer).

Therefore all amplification products will have at least 62 to 120 bp of terminal Alu sequences in them (depending upon whether a segment was the amplification product of priming from Alu-1 to Alu-1, Alu-1 to Alu-2, or Alu-2 to Alu-2). The second species of repeat sequences present in probe are those repeat sequences which happen to be located between Alu sequences which, along with the desired unique sequence, get amplified as a result of the inter-Alu-PCR. In order to more effectively block the Alu ends, Alu-1 and Alu-2 primers are to be used in PCR reactions with primers that recognize the arms of a plasmid containing the complete Alu sequence (BLUR2 (31)). This will amplify those same terminal Alu sequences that were amplified by the inter-Alu PCR. Those amplified terminal Alu sequences, along with low-Cot DNA (described above and which represents additional Alu segments and other species of repeat sequences present in the inter-Alu-PCR product), may be covalently linked to diazobenzyloxymethyl cellulose (32,33) and hybridized with the labeled probe (34,35) following nick-translation and biotinylization. Biotinylated fragments containing the repeat sequences will hybridize to those sequences bound to the cellulose and may be centrifuged out. Remaining biotinylated probe (containing only chromosome-specific unique sequences) will then be directly hybridized to metaphase spreads to detect the specific human chromosome regions of interest. An economical feature associated with the use of the diazonium cellulose with the chemically bonded repeat sequences is that the biotinylated fragments, attached to them after a reaction cleaning up the inter-Alu PCR reaction, can be removed by simply reheating the complex. This regenerates the diazonium cellulose with its bound repeat sequences for reuse in cleaning up more inter-Alu-PCR product.

Chronic myelogenous leukemia (CML) is a clonal disease that results in the selective expansion of Philadelphia chromosome positive late myeloid progenitor cells (44). At least 90–95% of CML are characterized by the Philadelphia chromosome (Ph) which is a shortened chromosome 22 that arises from a reciprocal translocation, t(9;22) (q34;q11) (45,46). Biotin-labeled painting probes generated by inter-Alu-PCR from human-rodent hybrids containing only the terminal half of the human chromosome 9 q-arm provides specific and unambiguous identification of the normal and rearranged chromosome 9 elements in even the most dismal metaphase preparations from CML patients (47). Such results suggest the possibility of identifying the translocating in non-dividing cells and therefore free analyses from biases associated with depending upon metaphase preparations.

This was first attempted using a combination of cosmid probes—one for 3'ABL sequences labeled for visualization in a red color and the other for 5'BCR sequences which would be detected as green through a double band-pass filter (48). Digitized images were collected with a cooled CCD camera and displayed after computer enhancement. A combination of the two colors indicated the presence of the Ph chromosome. The small size of the region detected by these probes do not make them reliable enough for large scale clinical use.

An alternative strategy is to use a single colored, labeled probe covering a sufficiently large region surrounding the translocation breakpoint of one of the involved chromosomes so that when applied to cell interphases with the translocation three bright hybridization signals would be observed—one from the unaltered chromosome, a second from the portion of the probed region retained following the translocation and a third from the probed region of the chromosome that was translocated. The presence of only two signals (from the two unrearranged chromosome) indicates normal cell interphases. If the probe, though large, is sufficiently small to identify well resolved domains in the interphase nucleus, this approach becomes technically less rigorous than the two-color, computer enhanced, digitized image approach and at the same time is more sensitive than using cosmid sized probes.

Recently Lengauer, et al. demonstrated use of a YAC clone (215 kb) containing the BCR gene to identify the Ph translocation in interphase CML cells (49). Inter-Alu-PCR product from the YAC showed that most interphase nuclei of a CML patient contained three signals while 90% of normal diploid cells had two signals as expected. Since these signals appeared as dots in the interphase nuclei there was a good possibility of false negatives missing some true targets due to incomplete hybridization) or false positives (counting artifactual spots). However, in a sufficiently large sample size it was expected that the presence of cancer cells in a population could be detected.

The inventors have used radiation hybrid E6B containing approximately 5 Mb of human DNA surrounding the ABL region of human chromosome 9 (50) as FISH probe and have evaluated its effectiveness in detecting the Ph chromosome translocation in polymorphonuclear cells (polys) of CML patients. Surprisingly, the larger size probe provides a clear, yet resolvable signal for detection of three domains of hybridization in CML interphases and two domains in normal cells. Non-cycling polys were selected as targets to avoid cells in stages of the cell cycle in which the domains to be visualized might not be expected to be well resolved (e.g., S-, and G2-phases).

While this invention has been described in terms of providing probe for specific regions of the human genome so that those areas can be visualized by in-situ hybridization in order to detect any possible alteration of those regions in cancer cells or cells of a developing embryo, such probe may also be used to isolate specific human genes located in those specific chromosomal regions. This is done by using probe made by any of the options above to screen tissue specific cDNA libraries. cDNA libraries are recombinant DNA molecules packaged usually into phage hosts in which the human DNA represents the human genes transcribed in those particular tissues. This technique will be extremely useful when genetic studies reveal, for instance, that the gene for Alzheimer's disease is located on a specific region of human chromosome 19. Then by making inter-Alu PCR probe for that specific region of human chromosome 19, brain cDNA libraries could be screened to isolate the human genes from that region for identification of candidate genes for the disease.

MATERIALS AND METHODS

BCR probe was obtained from Oncore (Gaithersburg, Md.). E6B radiation hybrid is available from Dr. Michael Siciliano, Dept. of Molecular Genetics, Box 45, University of Texas MD Anderson Cancer Center, 1515 Holcombe, Houston, Tex. 77030. The cells may also be obtained by the following procedure.

A radiation cell fusion procedure was used. The cell line 640-63a12, which contains human chromosome 9q (centromere-telomere) in a hamster background, was lethally irradiated with 4000–8000 rads of X-irradiation and fused using 50% PEG 1000 with cells from a Chinese hamster cell line deficient in HPRT activity (CHTG 49). Fused cell lines were selected by their ability to grow in media containing hypoxanthine, aminopterin, and thymidine (HAT). Some cell lines also underwent selection for expression of arginino-succinyl synthetase (ASS) activity. This was performed by growth n arginine-deficient DME medium supplemented with 0.6 mM citrulline ($arg^-cit^+$). Most rodent cell lines do not have ASS activity. Preliminary experiments demonstrated that the 640-63a12 cell line grew in the $arg^-cit^+$ medium and that CHTG 49 did not grow in the $arg^-cit^+$, indicating that ASS selection applied to hybrids 640-63a12/CHTG 49 could potentially identify those retaining the human ASS gene, which is on 9q34.

A total of 47 radiation-reduced cell lines were examined. Six of the cell lines grew in $arg^-cit^+$ medium and were positive by PCR analysis for retention of the human ASS gene. These 6 lines were further analyzed by PCR with primers for 11 $(GT)_n$ polymorphisms on 9q, which have been genetically and physically mapped. Only one cell line, E6B, was positive exclusively for markers from the 9q34 region (Table 1). E6B was further analyzed using primers for another 7 (GT)$_n$ repeat markers. E6B was positive only for markers in 9q34 (D9S63, D9S65, D9S66, and D9S125) and not for markers from elsewhere on 9q (D9S58, D9S123, and D9S124).

TABLE 1

PCR Analysis of Hybrid Cell Lines

| | | Cell line | | | | | |
|---|---|---|---|---|---|---|---|
| Marker | Location | B7-3 | B231A | B251B | E2B | E6B | E9B |
| MCT112 | q13 | + | − | − | + | − | − |
| D9S56 | q21 | + | + | − | − | − | + |
| D9S59 | q31 | + | + | − | − | − | − |
| GSN | q32 | − | − | − | − | − | − |
| D9S60 | q34 | − | − | + | + | + | + |
| D9S61 | q34 | − | − | + | − | + | − |
| D9S62 | q34 | | | | + | + | + |
| ABL | q34 | + | + | + | + | + | + |
| ASS | q34 | + | + | + | + | + | + |
| D9S64 | q34 | + | + | − | + | + | + |
| D9S67 | q34 | + | + | + | − | − | + |

Note. DNA markers are listed in centromeric to telomeric order.

The 6 cell lines were then analyzed by Southern blot hybridization with a panel of 10 probes from 9q (Table 2). E6B was positive for 6 markers from 9q34 (AK1 to ABO). The signal intensity of each positive marker for E6B was greater than that of an equal amount of DNA from 640-63a12, which contains one copy of 9q in a haploid hamster background. In contrast, the other hybrid lines always gave a weaker signal than 640-63a12, consistent with the presence of a single copy of the human DNA in a diploid/triploid hamster background in those lines.

TABLE 2

Southern Hybridization Analysis of Hybrid Cell Lines

| | | Cell line | | | | | |
|---|---|---|---|---|---|---|---|
| Marker | Location | B7-3 | B231A | B251B | E2B | E6B | E9B |
| Lamp 92 | q31 | + | + | + | − | − | − |
| L659 | q32 | | | | − | − | + |
| GSN | q33 | − | − | − | | | |
| AK1 | q34 | − | − | + | + | +$^a$ | + |
| ASS | q34 | + | + | + | + | +$^a$ | + |
| ABL | q34 | | | | + | +$^a$ | + |
| MCT136 | q34 | | | | | +$^a$ | |
| DBH | q34 | | | | + | +$^a$ | + |
| ABO | q34 | | | | + | +$^a$ | |
| EFD126.3 | q34 | + | + | + | − | − | + |
| MHZ21 | q34 | + | + | + | − | − | + |

$^a$Increased signal intensity relative to 640-63a12. Markers are listed in centromeric to telomeric order.

To determine the number of chromosome fragments retained in the hybrid cell lines, fluorescent in situ hybridization (FISH) was performed in metaphase chromosome spreads from five of the ASS-positive radiation-reduced cell lines using biotinylated total human DNA as a probe. Three of the cell lines (B7-3, B23-1A, and B25-1B) contained a small fragment of human DNA that was not associated with a hamster chromosome. All five contained one or two fragments of human DNA incorporated into hamster chromosomes. E6B showed two primary patterns of human DNA incorporation. About two-thirds of the E6B chromosome spreads showed a single human DNA fragment integrated into the short arm of a hamster chromosome. One-third showed a second, much less intensely staining fragment integrated more proximally on the short arm of the same hamster chromosome.

To characterize E6B further, FISH was performed on E6B metaphase chromosome spreads using cosmid DNA probes from 9q34. Five biotinylated cosmid probes (D9S60, D9S62, D9S63, D9S64, and D9S65) showed hybridization signals near the telomere of the short arm of a hamster chromosome (data not shown). This location is consistent with the site of integration of the more telomeric fragment of human DNA. A double fluorescent signal was sometimes seen on one or both chromatids, consistent with a duplication of that region of human DNA. Occasional spreads (approximately 5%) showed a second area of hybridization more proximally on the same chromosome arm. Biotinylated Alu-PCR products from E6B as a probe for FISH with human metaphases chromosomes were also employed. These Alu-PCR products hybridized to a single region of 9q, near the telomere, consistent with the location of 9q34.

A cosmid library was prepared from E6B DNA and screened with an Alu repeat probe. Approximately 1 of 1000 colonies from this library was positive. Fifteen of these cosmids were mapped using FISH to normal human metaphase chromosome spreads. All hybridized to 9q, with fractional length measurements ranging from 0.6 to 0.90, consistent with the fractional lengths of other cosmids previously mapped to 9q34. Forty of the cosmids were hybridized to metaphase chromosome spreads from a patient with chronic myelogenous leukemia and a (9;22) translocation. Thirteen of these cosmids gave signals on the derivative chromosome 22. This indicated that one-third of the human component of E6B is distal to the ABL1 locus on 9q34.

Since 1 in 1000 clones from the E6B cosmid library is human in origin, and the cell line is somewhat more than diploid in hamster DNA content, E6B was estimated to contain approximately 10 Mb of human DNA. The 6 loci tested between and including AK1 and ABO appeared to be represented by at least 2 copies. This suggests that E6B contains in duplicate about 5 Mb of human 9q34.

PREPARATION OF DNA TEMPLATE FROM HYBRID CELLS FOR INTER-Alu PCR

DNA template from hybrid cells may be prepared by several methods, two of which are described. The first method is most preferred in the practice of the invention.

1. DNA in Solution. DNA was isolated in traditional fashion by methods well known to those skilled in the art and are as described (36).
2. DNA in Agarose Plugs. Preparation of genomic DNA in agarose plugs was performed according to van Ommen and Verkerk (37). For PCR, the plugs were washed in 10 mM Tris-HCl pH7.5 for four changes at room temperature, 15 minutes each, then melted at 65° C. for 5 minutes. 10 mM Tris-HCl pH7.5 was added to a final volume of 500 µl. The size of the DNA was reduced by vortexing for 30 sec. before storage at 4° C. 10 µl was used for each PCR. This method also gave satisfactory results but was less preferred to method one above.

PCR Protocol

The consensus inter-Alu-PCR primers designed were:
Alu-1: GGATTACAGGYRTGAGCCA (seq id no: 1), and
Alu-2 : RCCAYTGCACTCCAGCCTG (seq id no:2)
where Y is either pyrimidine (T or C) and R is either purine (A or G). Therefore the Alu-1 primer is actually a cocktail composed of the 4 possible Alu-1 molecules (T at bp 11 and A at bp 12; T at bp 11 and G at bp 12; C at bp 11 and A at bp 12; and C at bp 11 and G at bp 12). Similarly Alu-2 is a cocktail of the 4 possible Alu-2 molecules with all possible combinations of alternative purines and pyrimidines at positions 1 and 5 respectively.

In a final volume of 50 µl, was added 100 ng genomic DNA in solution or 10 µl of melted agarose plug, 5 µl of 10×PCR buffer (100 mM Tris-HCL, pH 8.3, 500 mM KCL, 15 mM $MgCl_2$ and 0.01% gelatin), 0.2 mM dNTP, 50 pmoles of each of the two primers, and 1.25 units (0.25 µl of 5 unit/µl) Taq polymerase from Perkin-Elmer Cetus. The PCR reaction was conducted using a thermal cycler from Precision Scientific, Model GTC-1. After an initial 5 min incubation at 94° C., samples were subjected to 25 cycles as follows: 94° C. 1 min, 65° C. 1 min (a higher was used instead of the standard annealing temperature of 55° C. in order to amplify only human sequences in the presence of other mammalian Alu sequences, such as in a hybrid cell— for PCR from YACs, phage or any source where human Alus are the only ones present the standard annealing temperature would be preferable), and 72° C. 3 min. Finally an elongation of 10 min at 72° C. was conducted. One-tenth aliquots of each sample were run on gel. Primers and free nucleotides were removed with Centricon-100 (Amicon).

Evaluation of PCR Product on Agrose Gels 500 ng of PCR product was loaded on a 0.8% agarose gel (7 cm×7 cm) and run at 80–100 volts for 15–45 min. Ethidium bromide was incorporated into the gel and the running buffer by adding 5 µl ethidium bromide to 500 ml running buffer. Running buffer was:

Tris, 121.16 g
boric acid, 61.86 g
EDTA, 7.46 g
up to 4 l with water, pH brought to 8.3

Gels were photographed by Polaroid camera at f4.5 for 2 sec using #667 film while being transilluminated by UV light.

Nick translation to label the inter-Alu PCR product with biotin for use as probe Reaction components were from BRL nick translation kit, Cat. No. 8160SB. (BRL, Gaithersberg, Md.).

```
    x µl PCR product (1 ug DNA)
    5 ul A1
    2.5 µl 0.4 mM Bio-7-dATP
    y µl H2O 45 µl
add 5 µl solution C (DNA pol.1 and DNase)

50 µl
```

Product was mixed, spun down, and then incubated at 16° C. for 90 min. 5 µl stop buffer was added and the mixture then run through a Worthington Sephadex column to remove free nucleotides. A check for DNA was made using 100 ng on minigel. The size of inter-Alu PCR product ranged from 0.1–>4 kb and the size of the nick translation product ranged from 100–400 bp.

Slide Preparation

1. Freshly fixed (acetic acid-methanol) slides of cells in log phase growth were prepared by standard methods.
2. RNAse treatment. 100 ug/ml, 1 hr., moist chamber, 37° C., rinse in 4–6 changes in 2×SSC, dehydrate through ethanols.
3. Denature DNA. Immerse in 70% formamide (in 2×SSC) at 71° C. for 5 min. Dehydrate in ethanol on ice. Dry.

Probe Cocktail for In-Situ Hybridization—Preparation and Application

In an Eppendorf tube was added 400 ng biotinylated probe DNA, 20 ug of Cot 10 human DNA (see next paragraph) and 5 ug of sonicated salmon sperm DNA. The DNA was dried down, and resuspended in 5 µl $H_2O$ before adding 12.5 µl formamide, 2.5 µl 10×SSC, and 5 µl 50% dextran sulphate. Probe was denatured at 75° C. for 5 minutes, pre-anneal at 37° C. for 20 minutes. The probe was applied on one slide, covered with a 22×30 mm coverslip and Incubated at 37° C. overnight in moist chamber.

Washes were conducted at 41° C.: 3 changes in 50% formamide in 2×SSC for 3 min. each, then 5 changes in 2×SSC for 2 min each stirring vigorously. Storage was in the dark in BT buffer, pH 8.0.

Cot 10 human DNA was prepared from placental DNA, purchased from Sigma. It was dissolved in TE and sonicated to an average size of 500 bp. Then 20 mg of DNA was denatured and incubated at 65° C. in 2 ml 5×SSC until Cot10. The DNA solution was quickly chilled on ice and 10 fold excess of nuclease S1 buffer (33 mM NaAc, pH4.5 and 1 mM $ZnSO_4$) and 800 units of nuclease S1 were added. After 2 hours incubation was carried out at 37° C. to digest single-stranded DNA before removing nuclease S1 with proteinase K digestion. Finally the DNA was purified with phenol/chloroform extraction and ethanol precipitation.

Fluorescent Staining

The following steps were utilized in fluorescent staining procedures.

1. Drain and blot off BT buffer and add 55 µl 15% BSA in BT buffer and cover with plastic cover slip 5 min at room temp.
2. Peel off cover slip, drain fluid and put on 55 µl fluorescein avidin solution (2.5 µl fluorescein avidin (FA) and 247.5 µl 5% BSA in BT buffer). (That comes to 0.55 µl FA.) Cover with plastic cover slip, in moist chamber 37° C. for 1 hr.
3. Wash in BT buffer at 40° C. 3×. Store as before in dark in BT buffer at room temp.
4. Blot and apply 55 µl 5% goat serum in BT buffer and cover with plastic cover slips for 5 min. at room temp. Peel off cover slip, drain fluid and add 55 µl of biotinylated anti-avidin solution (12.5 µl biotinylated anti-avidin plus 237.5 µl 5% goat serum in BT buffer and recover with plastic cover slip). Incubate in moist chamber at 37° C. for 1 hr. and wash as in "3".
5. Add another layer of fluorescein avidin as in "2" above.
6. Repeat "3", "4", and "5" to put on a 3rd layer.
7. Wash and store as in "3".
8. Counterstain for 90 sec. in 2 µl/ml propidium iodide in deionized water. Mount with antifade solution (38).

Microscopy

Photomicrographs were obtained using a Zeiss Epi-illumination Photoscope with filter combination 48 77 09 and photographed on Kodak Ektachrome 160 with exposure times between 30 and 50 seconds.

The following examples are intended to illustrate the practice of the present invention and are not intended to be limiting.

Blood Samples and Cytogenetic Analysis

The bone marrow (BM) or peripheral blood (PB) samples used for this study were obtained as response evaluation procedures from patients on protocols approved by the University of Texas M.D. Anderson Cancer Center's Surveillance Committee. BM samples from normal HLA allo-BM transplant donors were used as controls. Two PB samples were from healthy laboratory volunteers.

Cytogenetic analysis was performed on freshly aspirated patient BM as well as PB cells from healthy laboratory volunteers. Metaphases were analyzed for G-bands using trypsin-Giemsa techniques as carried out in the clinical cytogenetics laboratory (51).

Probe for FISH was prepared from radiation hybrid E6B which has been shown to contain only approximately 5 Mb of human DNA from human chromosome band 9q34 as its only human genomic content. Molecular marker analysis has indicated that the human region retained extends from AK1 to ABO, which includes ABL, and that approximately ⅓ of the region is translocated to the Ph chromosome in CML patients (50). Methods for preparation of human specific FISH probe from hybrid cells by inter-Alu-PCR, biotin-labeling the probe, competitive hybridization blocking of repeat sequences, FISH, UV microscopy and photography as carried out in this laboratory have been meticulously described in Liu et al. (52)

Analysis was performed by enumeration of hybridization signals in polys. The percentage of cells with one through four signals was calculated from the total number of analyzable cells.

EXAMPLE 1

Selective Amplification of Human DNA with Alu-1 and Alu-2

The primers were tested for their specificity for amplification of human DNA. At standard conditions for PCR (which include annealing of primer to template DNA at 55° C.) both primer sets Alu-1 and Alu-2, either alone or in combination, amplified rodent as well as human DNA. This is demonstrated in Panel A of FIG. 1. The products of the PCR reaction conducted on the DNA from human HeLa cells (human) and CHO cells (Chinese hamster) were visualized after electrophoretic separation on an agarose gel. A smear of product (indicating DNA in a wide range of molecular weights (from 100 bp to 20,000 bp) was produced in CHO as well as human DNA. However, raising the annealing temperature to 65° C. successfully amplified human but not CHO DNA. This is indicated in Panel B of FIG. 1 where a wide size range of DNA was produced from human DNA but none from CHO.

EXAMPLE 2

Figure 2:
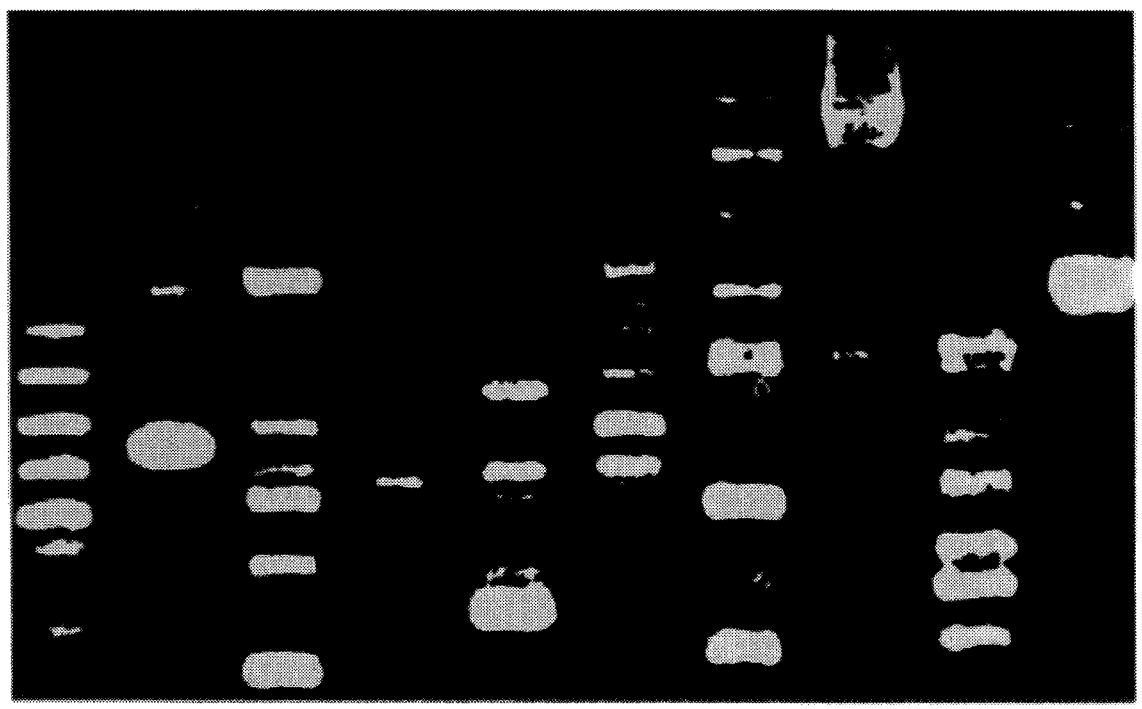
FIG. 2 shows an agarose gel separation of inter-Alu-PCR products after using the Alu-1/Alu-2 primer sets (O) or a published Alu PCR primer (N) on human genomic DNAs from a series of cosmids (numbered 1–5).

The efficiency of the Alu-1 and Alu-2 primer sets were compared with Alu-PCR primers TC-65 or 559 previously published (19) and used to generate in-situ hybridization probe (20). This was done by using a series of cosmids containing 20,000 bp to 40,000 bp of human DNA as substrate for PCR reactions and separating the products on agarose gels. The more efficient primers were expected to prime more frequently and therefore produce a wider spectrum of DNA bands from the cosmids. As shown in FIG. 2, Alu-1 and Alu-2 primers (O) produced a significantly greater number of bands of human genomic DNA than were produced using the previously published primer (N) from each cosmid.

EXAMPLE 3

PCR Production of Human Probe From Hybrid Cells

Figure 3:
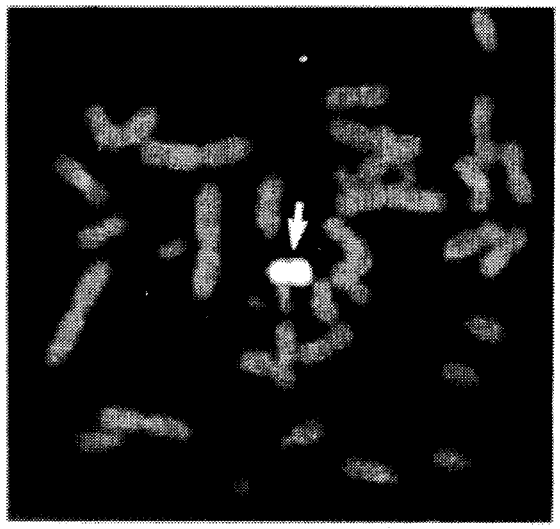
FIG. 3 is a photomicrograph of a metaphase from hybrid 5HL9-4, which contains human chromosome 19 as the only human genetic element, in-situ hybridized using total human DNA as probe. The arrow indicates the only fluorescing chromosome.

Cell line 5HL9-4 is a human×CHO somatic cell hybrid containing chromosome 19 as its only human genomic element (39). This is demonstrated in FIG. 3 where using total human DNA as in-situ hybridization probe on the cells revealed only a single human chromosomal element as brightly fluorescing. Conducting PCR with Alu-1 and Alu-2 as primers, at the annealing temperature (65° C.) specific for human DNA, produced a smear of human DNA from 100 bp to 20,000 bp in length. Therefore, using the specific hybrids and conditions for PCR, human specific probe for in-situ hybridization could be prepared from DNA of a hybrid cell in which the human DNA represented less than 5% of the total in the cell.

EXAMPLE 4

Painting of a Specific Human Chromosome

Inter-Alu-PCR DNA from 5HL9-4 was used for in-situ hybridization on a human metaphase cell after biotinylating the PCR product, blocking non-chromosome specific repeat sequences with low Cot DNA and visualizing the sites of hybridization with the avidin-fluorescence reaction. The results, shown in FIG. 4, clearly indicated human lymphocyte metaphases in which the only brightly fluorescing human genetic elements were the two human number 19 chromosomes. Significant fluorescence was present on only the two human number 19 chromosomes while fluorescence on other chromosomes was effectively quenched. Note the absence of fluorescence at the centromere of this and all other chromosome specific probe produced by inter-Alu-PCR. At this level of contraction, each chromosome arm of chromosome 19 appears as one large R-band.

EXAMPLE 5

Painting a Specific Chromosome Arm

Figure 5:
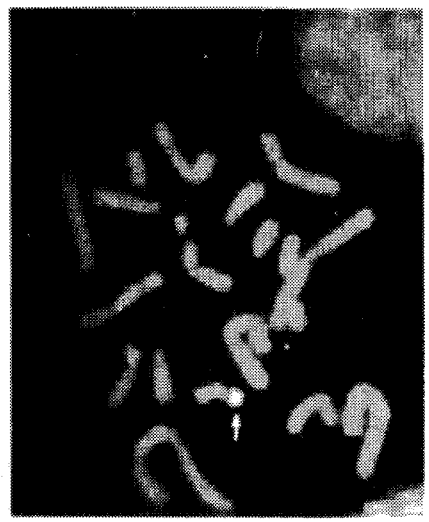
FIG. 5 is a photomicrograph of a metaphase of a hybrid cell (41XP91-3) containing the p-arm or human chromosome 16 as the only human genetic element following in-situ hybridization with total human DNA. The arrow indicates one small fluorescing fragment containing human DNA.
Figure 6:
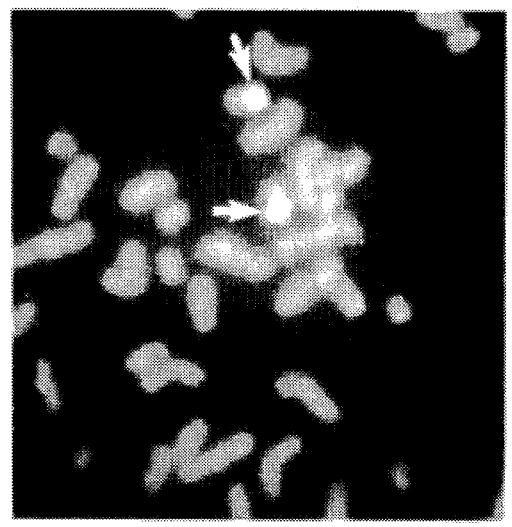
FIG. 6 is a photomicrograph of a human metaphase spread following in-situ hybridization with inter-Alu-PCR probe made from the hybrid (41XP91-3) containing the p-arm of human chromosome 16 as the only human genetic element. Arrows indicate both p-arms of human chromosome 16 as the only fluorescing elements.

The procedure described was used to paint only part of a human chromosome. FIG. 5 indicates a hybrid cell (41XP91-3) containing a fragment of a human chromosome. 41XP91-3 is one of a series of hybrid cells made between human xeroderma pigmentosum cells and the DNA repair deficient CHO cell line UV41. Hybrids were selected for the complementation of the missing DNA repair function in UV41 (selection in mitomycin C). Biochemical and molecular analysis of the hybrids indicated that the human repair gene complementing the lost function in UV41 must be on human chromosome 16 since genetic markers identifying the 16 were present in every hybrid while other human chromosomes were only randomly present (40). Furthermore, the analysis indicated that 41XP91-3 had markers only from the p-arm of chromosome 16 and contained no markers representing any other region of the genome. That, plus the cytogenetic analysis exemplified in FIG. 5, allowed us to concluded that the hybrid cell line contained only a portion of human chromosome 16 as its only human content. Probe was prepared and applied to human metaphases. As seen in FIG. 6 only the p-arm of chromosome 16 lights up.

EXAMPLE 6

Painting a Specific Sub-Region or Band of a Chromosome

Figure 7:
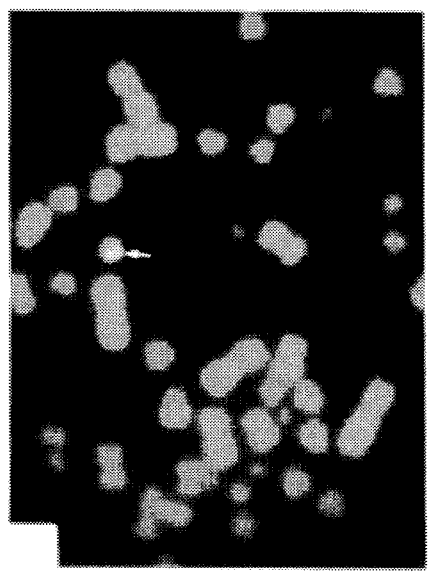
FIG. 7 is a photomicrograph of metaphase following in-situ hybridization with total human DNA on a hybrid cell line (2F5) containing from 1–2 Mb of human DNA from the q-arm of human chromosome 19 as the only human genetic element. That element is translocated onto a CHO chromosome. A small region of fluorescence on an otherwise non-fluorescent chromosome is indicated by the arrow.
Figure 8:
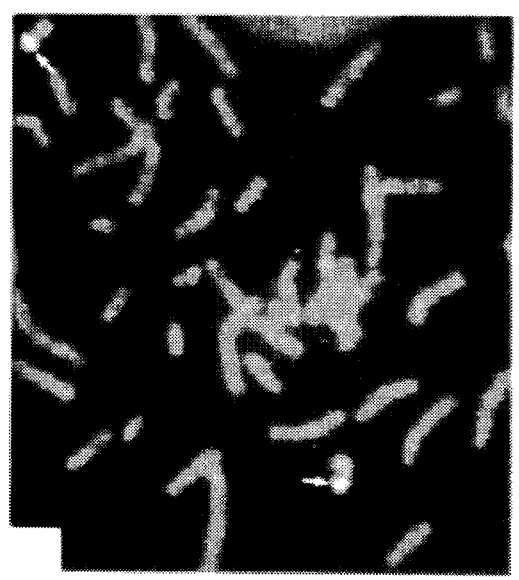
FIG. 8 is a photomicrograph of two human metaphase cells following in-situ hybridization with inter-Alu-PCR probe made from hybrid 2F5. Arrows indicate the location of narrow bands of fluorescence appearing only on both chromosome 19 q-arms.

Probe was prepared from a hybrid (2F5) containing only a small fragment of human genetic material attached to a CHO chromosome (FIG. 7). 2F5 was derived from a human×CHO hybrid (20XP3542-1-4) which was shown to have approximately 25 Mb of human DNA derived largely from a portion of human chromosomes 17 (41) and a small region from the q-arm (q13.3) of chromosome 19 in the vicinity of the DNA repair gene ERCC1 (42). 2F5 was prepared from 20XP3542-1-4 by X-irradiation of the former and hybridization back to the CHO cell line that was its original rodent parent (UV20). Radiation hybrids were selected for ERCC1 by growth in mitomycin C (43). Analysis of molecular markers retained in 2F5 indicated that it had lost all human DNA except the region of ERCC1 on chromosome 19 and that the total amount of human DNA in the hybrid was between 1 Mb and 2 Mb (D. Shaw, Cardiff, Wales, U.K., personal communication). The in-situ hybridization probe made by inter-Alu-PCR from 2F5 detected only band p13.3 on every human chromosome 17 in all human metaphases seen (over 50; e.g., FIG. 8).

EXAMPLE 7

Painting Specific Chromosomes With a Banding Pattern

Figure 9:
FIG. 9 and FIG. 10 are photomicrographs of two human metaphases following in-situ hybridization with inter-Alu-PCR probe made from the hybrid containing only human chromosome 7. The arrow indicates the location of two chromosomes with fluorescence in each cell. The fluorescence produces an R-banding on the chromosomes.
Figure 10:

Probe was prepared from a hybrid containing only a single human genetic element which molecular analysis indicated to be a human chromosome number 7. When probe was made from this hybrid and used for in-situ hybridization on human metaphases (FIGS. 9 and 10), the two chromosome 7s lit up in an R-banding pattern.

Figure 11:
FIG. 11 is a photomicrograph of a human metaphase following in-situ hybridization with inter-Alu-PCR probe made from DNA of a hybrid containing chromosome 5 as its only human genetic element. Note the presence of only two fluorescing chromosomes in the cell with the broad R-band pattern distinctive for human chromosome 5.

Probe was made from the DNA of a hybrid known to contain only chromosome 5 (obtained from L. Nagaragian, Department of Hematology, University of Texas M.D. Anderson Cancer Center, Houston, Tex.). As shown in FIG. 11, chromosome 5 is the only painted element in a human metaphase spread. The distinctive R-band pattern is identifiable in this somewhat overly contracted state.

Figure 12:
FIG. 12 and FIG. 13 are photomicrographs of human metaphases following in-situ hybridization with inter-Alu-PCR probe made from a hybrid containing chromosome 17 as its only human genetic element. Both chromosome 17s are lit up in both figures. Where the chromosome is more condensed (FIG. 12) the R-bands are closer together and the R-banding pattern is not obvious. The chromosomes are identified in poorly spread metaphases as shown in FIG. 13.
Figure 13:

Inter-Alu-PCR probe made from a hybrid containing only human chromosome 17 (obtained from David Ledbetter, Baylor College of Medicine, Houston, Tex.) specifically lit up chromosome 17 in human metaphase spreads (FIG. 12). The chromosome is small and highly contracted in this metaphase. As seen in FIG. 13, the R-band patterns are resolved and the chromosome 17s are observed in metaphases where chromosomes are not well spread out.

Figure 14:
FIG. 14 is a photomicrograph of a human metaphase following in-situ hybridization with inter-Alu-PCR probe made from a hybrid containing chromosome 3 as its only human genetic element. Both chromosome 3s are the only fluorescing elements in the broad R-band pattern, with a dark centromeric region characteristic of human chromosome 3.

Probe made from a hybrid containing human chromosome 3 as the only human element was characterized and obtained from Dr. Susan Naylor (University of Texas Health Science Center at San Antonio, Tex.). When applied to a human metaphase spread this probe specifically hybridized to human chromosome 3 in an R-banded pattern (FIG. 14) supporting the hypothesis constructed after observing the results with the chromosome 7 probe.

In addition to the human chromosomes presented in the examples, the method has been used to paint R-band patterns on chromosomes 9 and 16.

EXAMPLE 8

Detection of Chromosomal Abnormalities

From the examples shown, it is clear that translocations between one chromosome and another will be obvious and easily detected using a chromosome specific probe. For instance, where a translocation existed between one of the chromosome 19s and one of the 17s, probe from the 19 would readily detect a single, entirely fluorescing chromosome (the 19 not involved in the translocation) and two other chromosomes with only portions fluorescing (the 19 with a piece of the 17 and the 17 with a piece of the 19). By the same token, it will be even easier to identify monosomies (a single fluorescing chromosome instead of two in the cell), and trisomies (three fluorescing chromosomes). A special advantage in working with probes for only a portion of a human chromosome or which light up a banding pattern on a chromosome is that it will enable the identification of inversions and also the specific sites of deletions and translocations.

Detection of an Inversion

Figure 15:
FIG. 15 is a photomicrograph of a human leukemic cell with a known chromosome 16 inversion after in-situ hybridization with inter-Alu-PCR probe made from a hybrid containing only the p-arm of chromosome 16. At the bottom of the field is the unaffected chromosome 16 with only the p-arm fluorescent. Note the inversion chromosome with fluorescence not only the end of the p-arm but also in the middle of the q-arm (arrow).

A chromosome 16 p-arm specific probe as described in Example 4 above was used to identify the inversion 16 chromosome associated with acute nonlymphocytic leukemia. Since the inversion breakpoint on the p-arm cuts right through the painted region of the chromosome, the inversion chromosome was readily identified as a chromosome having fluorescence at the end of the p-arm and also in the middle of the q-arm (FIG. 15).

Detection of the Site on a Deletion

Figure 16:
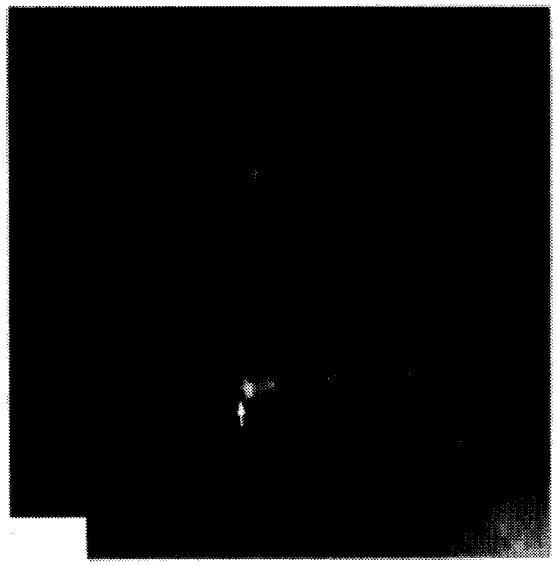
FIG. 16 is a photomicrograph of a metaphase from a leukemic cell line with a known chromosome 7 deletion following in-situ hybridization with the inter-Alu-PCR probe made from a hybrid cell containing human chromosome 7 as its only human DNA content. In addition to a banded fluorescing intact chromosome 7, a second banded fluorescing chromosome 7 deleted distal to the bright band on the proximal region of the long arm is shown indicated by the arrow.
Figure 17:
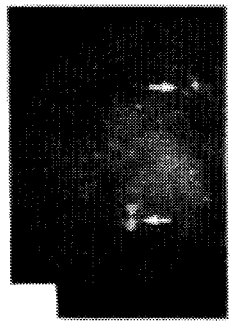
FIG. 17 and FIG. 18 are photomicrographs of normal human interphase nuclei following in-situ hybridization with the inter-Alu-PCR probe made from hybrid 2F5 which contained only 1–2 Mb of human DNA from band q13.3 of human chromosome 19. Notice the bright, punctate fluorescence resolving each of the domains occupied by these regions of chromosome 19 in the interphase cells.

Chromosome 7 specific probe which lit up a banding pattern on chromosome 7 was used to identify the location of a deletion on the 7 associated with an AML cell line KB-1 (provided by Jan Liang, Division of Laboratory Medicine, University of Texas M.D. Anderson Cancer Center, Houston, Tex.). When applied to the cell, the number 7 chromosomes were immediately identifiable with the normal 7 quite distinct from the deleted 7. The site of the deletion was readily detected as just distal to the most proximal bright band on the q-arm as shown in FIG. 16.

EXAMPLE 9

Figure 20:
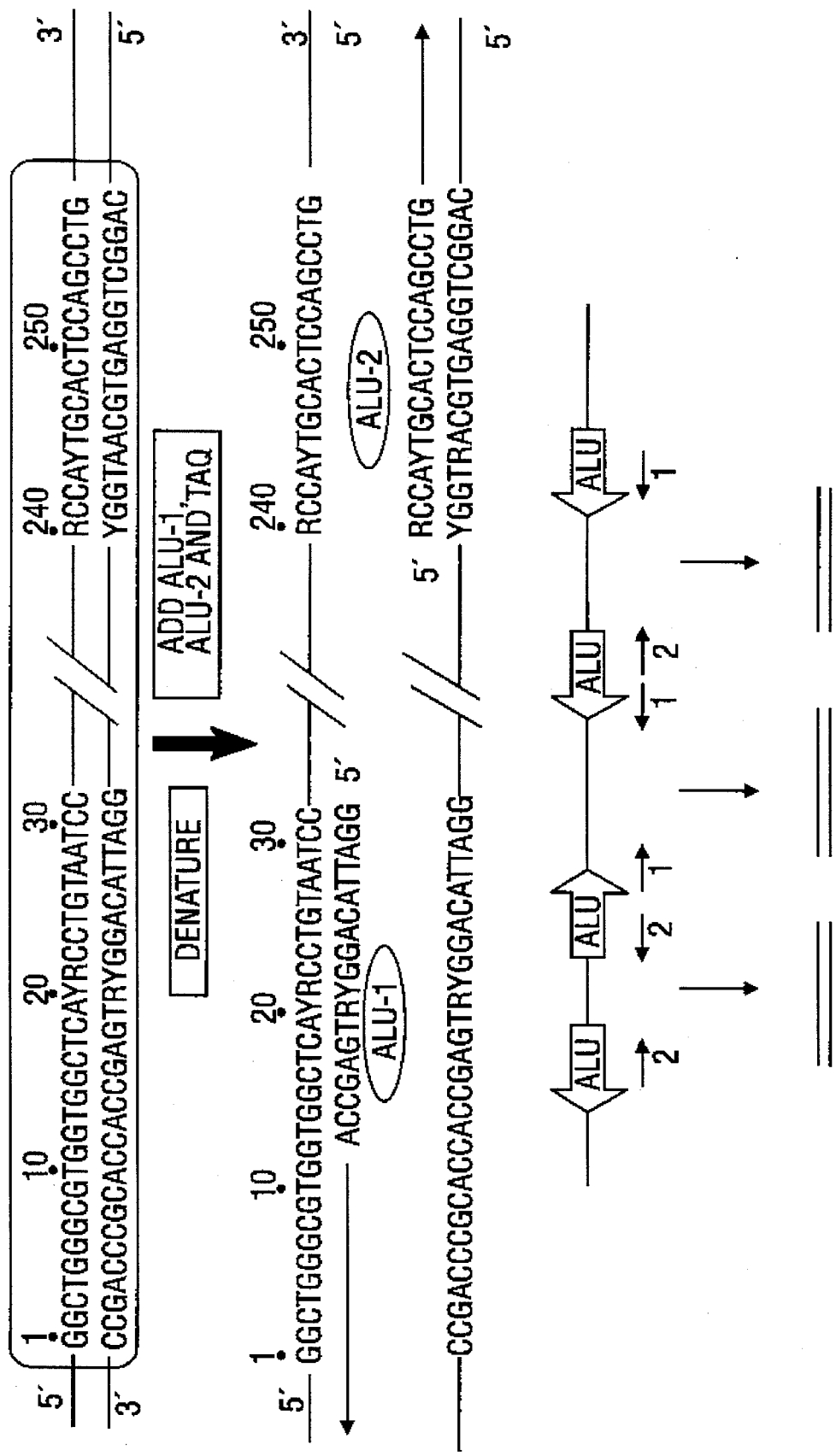
FIG. 20 illustrates amplification of inter-Alu regions using Alu-1 and Alu-2 primers.
Figures 21A, 21B:
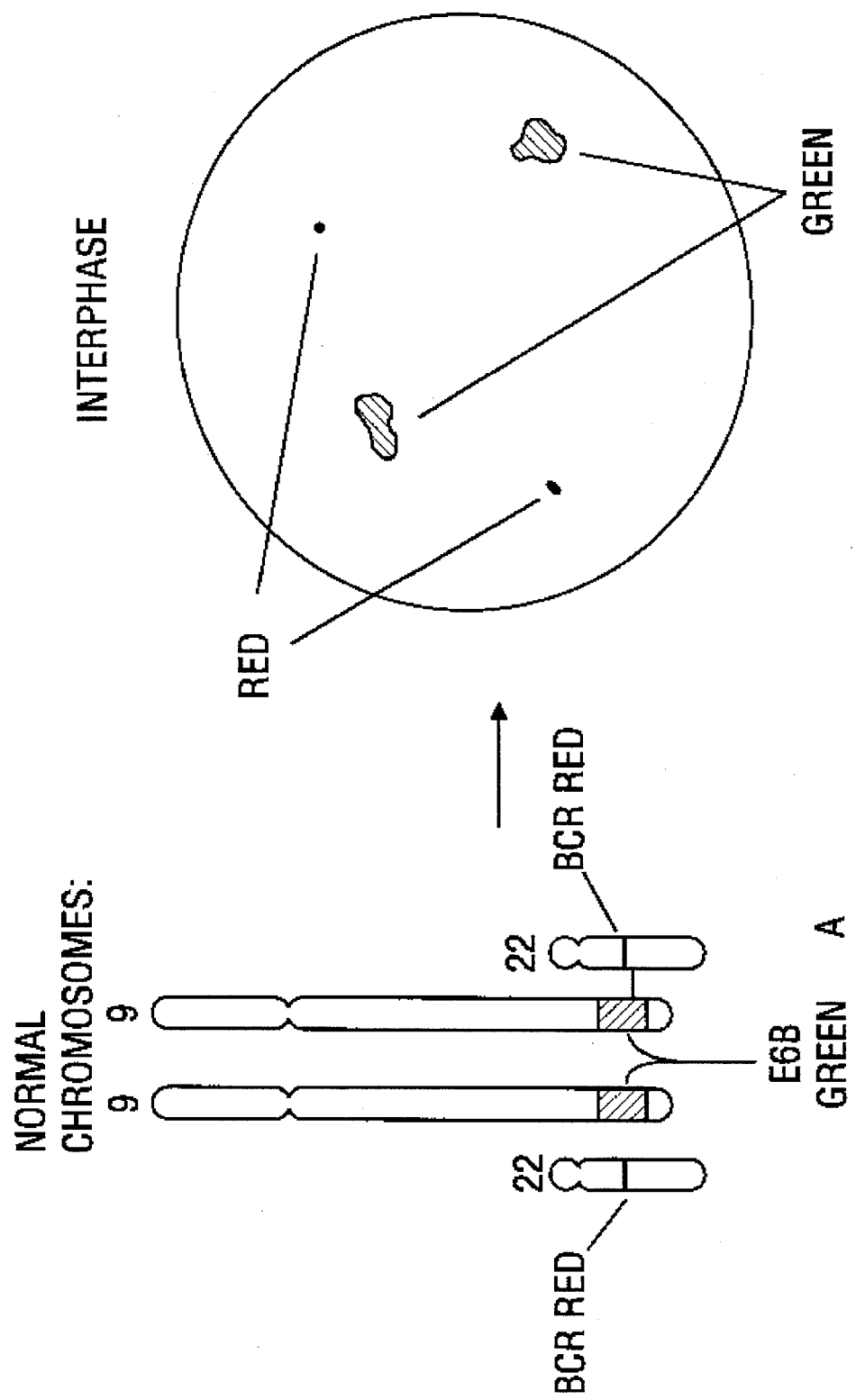
FIGS. 21A, 21B, 21C and 21D show a cartoon of normal interphase human 9 and 22 chromosomes hybridized with labeled probes specific for each chromosome (FIG. 21A) and the same chromosomes after translocation between chromosomes 9 and 22 (FIG. 21C).
Figures 21C, 21D:
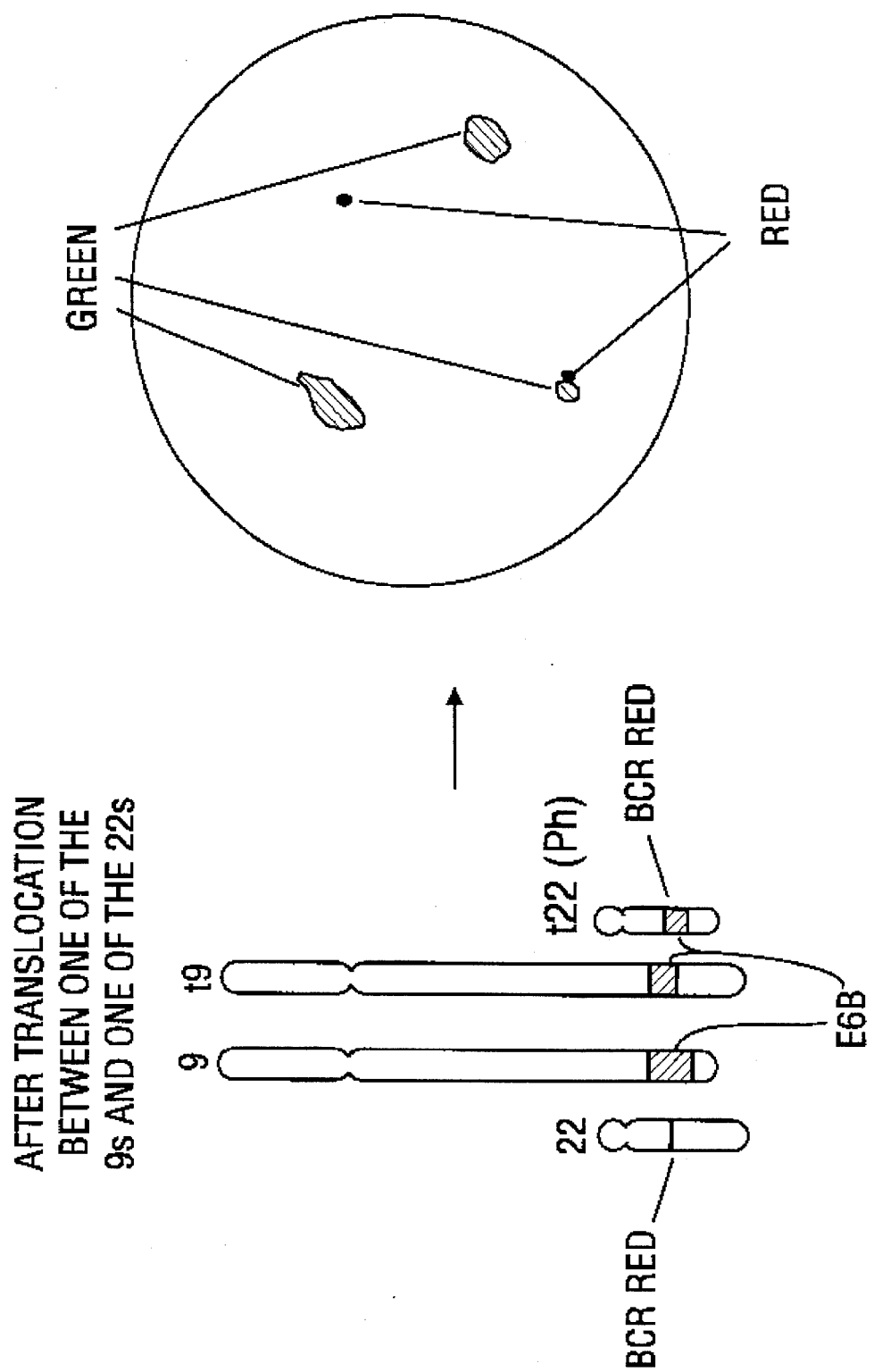

Identification of Chromosome Regions in Interphase Nuclei Chromosome Regions in Normal Cell Interphases In the interphase nuclei, chromosomes are "unwound" or drawn out to the extent that they are no longer individually identifiable. Using the probes that are specific for an entire human chromosome, it is possible to identify but difficult to resolve the "domains" within an interphase nucleus in which the particular chromosomes exist. However, by using probe made from a hybrid containing a highly limited region of a particular chromosome, such domains are clear, bright and highly resolved. This is demonstrated by using probe made from hybrid 2F5 (described in Example 6 above) which contains only 1–2 Mb of human DNA from band q13.3 of human chromosome 19. As seen in FIG. 20, such probe gives clear resolution of the chromosomal region in interphase nuclei.

Chromosomal Abnormalities in Interphases

Figure 19:
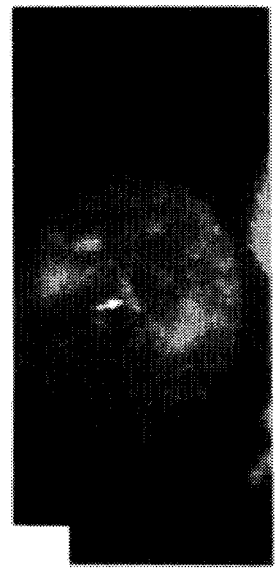
FIG. 19 is a photomicrograph of an interphase nucleus of a human leukemic cell with a known chromosome 16 inversion after in-situ hybridization with inter-Alu-PCR probe made from a hybrid containing only the p-arm of chromosome 16. Two bright domains of hybridization are interrupted by non-fluorescence as indicated at the arrow.
Figure 18:
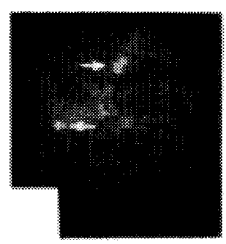

Probe for any normal chromosome will identify two domains in an interphase nucleus. Where there has been a translocation involving a chromosome three, poorly resolved domains may be visible. Three domains were expected from the inversion 16 chromosome described in Example 8a above. FIG. 19 shows that by using probe for only part of the chromosome in such an interphase nucleus, the normal 16 appeared as a single elongated domain of fluorescence representing the uninvolved 16p arm. Also seen was a second elongated domain divided by a zone of non-fluorescence as expected for the chromosome bearing the inversion.

EXAMPLE 10

Following FISH with probe from E6B on BM and PB cells from nine unaffected individuals, polys were readily identified by their distinctive shape. The vast majority of such interphase nuclei (whether from the BM or PB preparations) had two domains of staining (FIG. 1a and Cases 1–9 on Table 1). Occasional metaphases encountered on these preparations confirmed that these two domains originated from the q34 regions of the two chromosome 9s in each cell (FIG. 1b).

Figure 1B:
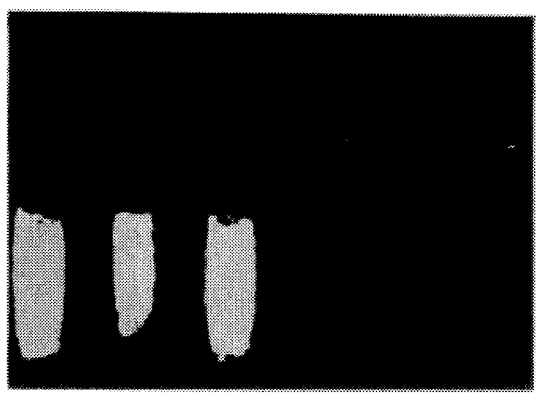

Quite distinctively, the polys from the BM and PB cells from six CML patients had three domains of staining (FIG. 1b and Cases 10–15 on Table 1). Not only were the number of FISH domains in the CML polys consistent with the hypothesis that the signal from one of the chromosome 9s had been split, but lesser intensity of one of the three domains (arrows on FIG. 1c) was consistent with the expectation that the region translocated was <⅓ of the DNA recognized by the probe on human chromosome 9 (50). This was confirmed in every metaphase encountered wherein signal was detected from the q34 regions of the two chromosome 9s and much weaker signal detected from a third source, the Ph chromosome (FIG. 1d). Conventional cytogenetics indicated that 100% of the 20 to 25 well spread metaphase cells studied/patient were Ph+. Need some sort of statement on the % age of the cells that were polys and the % age of the non-polys that were ambiguous. Also, need some data on the number of domains in the non-polys relative to the status of the patients from which they were drawn.

We conclude that FISH probe from E6B is a powerful and valid tool for identifying the presence of the Ph chromosome in either BM or PB preparations of polys. Analysis of the number of domains of staining in normal polys indicated only a 3% false positive rate (as indicated by the presence of >two domains) and a false negative rate (<two domains) of 5%. The presence of over 12% of the CML polys with <three domains, more than double the false negative rate, indicated that the method will detect a minority of normal cell sin a CML population. As indicated by the standard metaphase cytogenetic results above, such cells would not normally be detected. From that, one can conclude that the method will similarly be able to detect a minority of Ph+cells in a sufficiently large population containing predominantly normal cells.

DISCUSSION

The percentages of polys from normal and CML individuals with <2, 2, and >2 domains of staining using probe recognizing a genomic domain that overlaps the region of a breakpoint involved in the formation of the Ph chromosome obtained here were similar to that obtained by Lengauer et al. using a BCR YAC as probe (49). Results using the larger probe from the radiation hybrid on polys were highly repeatable and gave a lower frequency of false positives (3% vs 6%) than reported using the YAC probe. Most importantly, it was clearly demonstrated by the percentage of cells with >2 domains of hybridization (88%) vs. the standard cytogenic results, which indicated that 100% of the cells were Ph+, that the frequency of cells carrying a cytogenetic abnormality in a cell population may be distorted by depending on results from cells caught in metaphase. There are many reasons why this should be true. The most obvious, and relevant to the question of the usefulness of this procedure in the management of CML, is that many cancer cells may be in a $G_o$ state at the time of analysis in the tissue being examined and may not be available for metaphase cytogenetic analysis. Therefore, the procedure, when combined with PCR analysis (53) should find application to questions associated with quantitation of minimal residual disease, lineage analysis, effectiveness of purging samples for autologous BMT, monitoring the effects of therapy, etc.

However, interphase FISH with E6B does have its limitations. At present it appears as though the signal generated by the large probe while very efficient for resolving the domains in polys is often diffuse in other cell types which may include more immature cycling cells. Use of the probe on populations of cells sorted according to their differentiational state or lineage types should help in interphase analyses and identification of cell types involved in CML. Since cycling cells eventually enter metaphase (and since this probe can clearly recognize the translocation event in even the poorest of metaphases) FISH analyses of both interphase and metaphase cells should now be able to give a more accurate picture of the frequency of Ph+ cells in patient material.

EXAMPLE 11

Philadelphia chromosome (Ph), the result of a reciprocal translocation t(9;22)(q34;q11), can be detected in 95% of CML. Fluorescence in situ hybridization (FISH) probe (E6B) derived only from the 9q34 region was tested to determine if it was small enough to resolve the region in interphase nuclei yet large enough to readily detect a third domain of hybridization (due to the split in the 9q34 region) in Ph+ cells.

The probe was shown to readily detect the Ph chromosome in CML cells, however, data from normal cells suggested a false positive (detection of three domains when only two should be present) rate of 3–4%.

Combining the probe with a probe identifying the portion of chromosome 22 (BCR) (source: Oncor, Inc.) remaining attached to its centromere after the translocation in two-color FISH, allowed verification of a third domain being the result of a translocation. This reduced the false positive rate to <1%.

These results indicated that the two-color FISH system described was an effective means of monitoring minimal residual disease since large numbers of non-dividing cells can be scored for a low frequency of Ph+ cells.

Inter-Alu-PCR of DNA from an interspecific hybrid cell containing band 9q34 as its only human genomic content produced probe (E6B) for FISH which specifically painted only that region of the human genome when applied to normal human metaphase cells (FIG. 1A). In normal interphase cells E6B generally detects two domains of hybridization reflective of the two 9q34 regions in the cell (FIG. 1B).

When applied to CML cells, in addition to signal on the unaffected chromosome 9, the signal is split between the affected chromosome 9 and the Ph chromosome (FIG. 1D) resulting in three signals in cells with the Ph chromosome. Three signals are also detected in interphase nuclei of CML cells (FIG. 1C).

The number of signals in normal and CML bone marrow and peripheral blood interphases was enumerated. Results are presented below in Table 3.

TABLE 3

% bone marrow (BM) and peripheral blood (PB) cells from normal and CML individuals with one - four domains hybridization after FISH with inter-Alu-PCR product from E6B.

% cells having the following # of domains:

| Individuals | 1 | 2 | 3 | 4 | Total # counted |
|---|---|---|---|---|---|
| Normals | | | | | |
| Case 1 (BM) | 9 | 88 | 2 | 0 | 235 |
| Case 2 (BM) | 5 | 91 | 2 | 2 | 128 |
| Case 3 (BM) | 4 | 90 | 3 | 3 | 139 |
| Case 4 (BM) | 4 | 92 | 2 | 2 | 168 |
| Case 5 (PB) | 8 | 91 | 1 | 0 | 100 |
| Case 6 (PB) | 2 | 93 | 3 | 2 | 100 |
| Case 7 (BM) | 5 | 94 | 1 | 0 | 149 |
| Case 8 (BM) | 2 | 96 | 1 | 0 | 138 |

TABLE 3-continued

% bone marrow (BM) and peripheral blood (PB) cells from normal and CML individuals with one - four domains hybridization after FISH with inter-Alu-PCR product from E6B.

% cells having the following # of domains:

| Individuals | 1 | 2 | 3 | 4 | Total # counted |
|---|---|---|---|---|---|
| Case 9 (BM) | 7 | 94 | 2 | 0 | 163 |
| Mean | 5.0 ± 1.9 | 92.0 ± 1.8 | 1.8 ± 1.0 | 1.3 ± 0.6 | 147 ± 30 |
| CMLs | | | | | |
| Case 10 (PB) | 4 | 7 | 88 | 2 | 199 |
| Case 11 (BM) | 4 | 6 | 88 | 2 | 125 |
| Case 12 (BM) | 2 | 12 | 86 | 0 | 150 |
| Case 13 (BM) | 3 | 11 | 86 | 3 | 140 |
| Case 14 (BM) | 2 | 7 | 89 | 3 | 196 |
| Case 15 (BM) | 6 | 13 | 79 | 2 | 86 |
| Mean | 3.4 ± 1.1 | 9.1 ± 2.5 | 86.0 ± 2.3 | 1.5 ± 0.7 | 149 ± 32 |

Results indicated that the probe is highly effective but that the 3–4% of normal cells with more than two domains might be a problem in detecting minimal residual disease.

To validate the third domain of staining as being due to a translocation, two-color FISH was conducted. BCR probe labeled with digoxigenin (from ONCOR) gives a red fluorescence to two regions in every cell. This was combined with biotin labeled E6B probe giving a yellow-green color.

When applied to normal interphases and viewing only E6B labeling (by using only a single pass filter allowing only the green-yellow fluorescence through) occasionally more than two domains of hybridization are seen in a nucleus.

By viewing the same filed with a dual pass filter (also allowing the viewing of the red fluorescence) it can be seen that in the same interphases the red dots do not overlay the yellow-green ones indicating that the third domains are not due to translocations.

When the same experiment is done on CML cells notice that the third domain of yellow-green fluorescence seen with a single pass filter is usually overlaid by a red dot when the dual pass filter is used to view the same field.

A second series of normal and CML marrows were studied for numbers of E6B domains in which more than two E6B domains was only scored when verified by overlap with BCR. The data are scored in Table 4 below:

TABLE 4

Number of bone marrow cells from normal and CML individuals with from one to four verified (with BCR) domains of E6B hybridization.

% cells having the following # of domains

| Individuals | 1 | 2 | 3 | 4 | Total | % >2 |
|---|---|---|---|---|---|---|
| Normal 1 | 25 | 363 | 0 | 1 | 389 | 0.25 |
| Normal 2 | 29 | 555 | 3 | 2 | 589 | 0.85 |
| Normal 3 | 38 | 478 | 1 | 0 | 517 | 0.19 |
| Normal 4 | 23 | 359 | 2 | 1 | 385 | 0.78 |
| Normal 5 | 49 | 532 | 2 | 1 | 584 | 0.51 |
| Norm. Tot. | 164 | 2287 | 8 | 5 | 2464 | 0.53 |
| Norm. % | 6.6 | 92.8 | 0.32 | 0.20 | — | 0.53 |
| CML 1 | 27 | 104 | 410 | 2 | 543 | 75.9 |
| CML 2 | 24 | 105 | 442 | 3 | 574 | 77.5 |
| CML 3 | 26 | 113 | 322 | 2 | 463 | 70.0 |
| CML 4 | 28 | 79 | 292 | 2 | 401 | 73.3 |
| CML 5 | 28 | 75 | 256 | 1 | 360 | 71.4 |
| CML Tot. | 133 | 476 | 1722 | 10 | 2341 | 74.0 |
| CML % | 5.7 | 20.3 | 73.6 | 0.42 | — | 74.0 |

* an additional 133 (5.1%) of the cells from normals and 223 (8.7%) of cells from CML marrows were judged not scorable for a variety of reasons: domains of staining too diffuse, insufficient signal in that area of the slide, smushed cells.

The higher frequency of unscorable cells from CML marrows is probably reflective of a higher proportion of cells from that source in the S phase of the cell cycle where signal would be more diffuse.

These results show that E6B FISH probe can detect Ph+ metaphase and interphase cells. Combining the probe for two-color FISH with BCR cosmids reduces false Ph positives in interphase cells to <1%. The real frequency of Ph+ cells in the marrow of CML patients judged 100% Ph+ based on standard cytogenetics is approximately 74%.

PROPHETIC EXAMPLE 12

The present example outlines the procedure contemplated by the Applicants to be useful for the isolation of genes that have been localized to a known region of the genome.

Probe is made from a specific region of the human genome where the gene of interest is known to be localized (via classical genetic mapping studies in families where that gene is known to be segregating, for example). A gene demonstrated to map into the band q 13.3 of chromosome 19, for example, is screened from cDNA libraries made from genes expressed in the human brain using inter-Alu-PCR probe made from the hybrid 2F5 (which retains band 19q13.3 as its only human genetic material). This will result in isolation of human brain genes from the genome region in which the desired gene is known to exist, providing candidate genes for the gene of interest. Isolation of such a gene would be viewed as important in the characterization, diagnosis, counselling and treatment of any disease associated with that gene.

FIG. 20 is a schematic illustration of the invention. In order to illustrate a particular example of how the primer sets work, a human Alu repeat sequence is shown in FIG. 20A. FIG. 20B illustrates how nonrepeat DNA regions are selectively amplified. Although the figure is illustrated using human Alu repeat segment, the same general scheme applies to the preparation of chromosomal specific DNA probes using other species specific repeat sequences.

The present invention has been described in terms of particular embodiments found by the inventors to comprise preferred modes of practice of the invention. It will be appreciated by those of skill in the art that in light of the present disclosure numerous modifications and changes can be made in the particular embodiments exemplified without departing from the intended scope of the invention. For example, primers and primer sets to repeat sequences other than Alu could be designed using the principles set forth without affecting the intended scope of the invention. All such modifications are intended to be included within the scope of the claims.

REFERENCES

The entire text of copending patent application Ser. No. 07/627,945 filed Dec. 13, 1990 is incorporated herein by reference without disclaimer.

The references listed below are incorporated herein by reference to the extent they supplement, explain, provide a background for or teach methodology, techniques and/or compositions employed herein.

1. Trent, J. M., Y. Kaneko and F. Mitelman, 1989. Report of the committee on structural chromosome changes in neoplasia. Cytogenet. Cell Genet. 51:533–562.
2. Harper, P. S., J. Frezal, M. A. Ferguson-Smith and A. Schinzel, 1989. Report of the committee on clinical disorders and chromosomal deletion syndromes. Cytogenet. Cell Genet. 51:563–611.
3. Rowley, J. D., 1973. A new consistent chromosomal abnormality in chronic myelogenous leukaemia identified by quinacrine fluorescence and Giemsa staining. Nature 243:290–293.
4. de Klein, A., A. G. van Kessel, G. Grosveld, C. R. Bartrum, A. Hagemeijer, D. Bootsma, N. K. Spurr, N. Heisterkamp, J. Groffen and J. R. Stephenson, 1982. A cellular oncogene is translocated to the Philadelphia chromosome in chronic myelogenous leukemia. Nature 300:765–767.
5. Heisterkamp, N., J. R. Stephenson, J. Grofen, P. F. Hansen, A. de Klein, C. R. Bartram and G. Grosveld, 1983. Localization of the c-abl oncogene adjacent to a translocation breakpoint in chronic myelogenous leukemia. Nature 306:239–245.
6. Seabright, M. 1971. A rapid banding technique for human chromosomes. Lancet 2:971–972.
7. Sumner, A. T., H. Evans and R. Buckland, 1971. New technique for distinguishing between human chromosomes. Nat. New Biol 232:31–72.
8. Lichter, P., T. Cremer, J. Borden, L. Manuelidis and D. C. Ward, 1988. Delineation of individual human chromosomes in metaphase and interphase cells by in-situ suppression hybridization using recombinant DNA libraries. Hum. Genet. 80:224–234.
9. Pinkel, D., J. Landegent, C. Collins, J. Fuscoe, R. Segraves, J. Lucas and J. Gray, 1988. Fluorescence in-situ hybridization with human chromosome-specific libraries: detection of trisomy and translocations of chromosome 4. Proc. Natl. Acad. Sci. USA 85:9138–9142.
10. Lichter, P., T. Cremer, C. -J. Chang Tang, P. C. Watkins, L. Manuelidis and D. C. Ward, 1988. Rapid detection of human chromosome 21 aberrations by in-situ hybridization. Proc. Natl. Acad. Sci. USA 85:9664–9668.
11. Pinkel, D., T. Staume and J. W. Gray, 1986. Cytogenetic analysis using quantitative, high sensitivity, fluorescence hybridization. Proc. Natl. Acad. Sci. USA 83:2934–2938.
12. Zhao, L., W. -L. Kuo, D. Pinkel, J. Gray, A. Deisseroth, J. Trujillo and J. C. Liang, 1990. Detection of t(9;22) in chromonic myelogenous leukemia by fluorescence in-situ hybridization with chromosome-specific composite probes. Am. J. Hum. Genet. 47:A26.
13. Kuo, W. -L., T. Bryndorf, L. -C. Yu, M. Poggensee, D. Pinkel, J. Liang, I. C. Tsai, C. W. Yu, D. -L. Day-Salvatore, L. Sciorra, M. -L. Lee and J. W. Gray, 1990. Clinical cytogenetic diagnosis with chromosome-specific DNA probes. Am. J. Hum. Genet. 47:A119).
14. Le Beau, M. M., R. A. Larson, M. A. Bitter, J. W. Vardiman, H. M. Golomb and J. D. Rowley, 1983. Associations of an inversion of chromosome 16 with abnormal marrow eosinophils in acute myelomonocytic leukemia. N. Engl. J. Med. 309:630–636.
15. Jelinek, W. R., T. P. Toomey, L. Leinwand, C. H. Duncan, P. A. Biro, P. V. Chaudary, S. M. Weissman, C. M. Rubin, C. M. Houck, P. L. Deininger and C. W. Schmid, 1980. Ubiquitous interspersed repeated sequences in mammalian genomes. Proc. Natl. Acad. Sci. USA 77:1398–1402.
16. Breukel, C., J. Wijnen, C. Tops, H.v/d Klift, H. Dauwerse and P. Meera Khan, 1990. Vector-Alu PCR: a rapid step in mapping cosmids and YACs. NAR 18:3097.
17. Brooks-Wilson, A. R., P. N. Goodfellow, S. Povey, H. A. Nevanlinna, P. J. de Jong and P. J. Goodfellow, in press. Rapid cloning and characterization of new chromosome 10 DNA markers by Alu element-mediated PCR. Genomics.
18. Cotter, F. E., G. M. Hampton, S. Nasipuri, W. F. Bodmer and B. D. Young, 1990. Rapid isolation of human chromosome-specific DNA probes from a somatic cell hybrid. Genomics 7:257–263.
19. Nelson, D. L., S. A. Ledbetter, L. Corbo, M. F. Victoria, R. Ramirez-Solis, T. D. Webster, D. H. Ledbetter and C. T. Caskey, 1989. Alu polymerase chain reaction: a method for rapid isolation of human-specific sequences from complex DNA sources. PNAS 86:6686–6690.
20. Glover, T. W., B. K. Hall and E. Legius, 1990. Construction of irradiation-reduced hybrids for human chromosome 3 and characterization by IRS-PCR (interspersed repetitive sequence PCR) analysis. Am. J. Hum. Genet. 47:A91 (ABSTRACT).
21. Kievits, T., P. Devilee, J. Wiegant, M. C. Wapenaar, C. J. Cornelisse, G. J. B. van Ommen and P. L. Pearson, 1990. Direct nonradioactive in-situ hybridization of somatic cell hybrid DNA to human lymphocyte chromosomes. Cytometry 11:105–109.
22. Dauwerse, J. G., T. Kievits, G. C. Beverstock, D. van der Keur, E. Smit, H. W. Wessels, A. Hagemeijer, P. L. Pearson, G. -J. B. van Ommen and HM. H. Breuning, 1990. Rapid detection of chromosome 16 inversion in acute nonlymphocytic leukemia, subtype M4: regional localization of the breakpoint in 16p. Cytognet. Cell Genet. 53:126–128.
23. Tkachuk, D. C., C. A. Westbrook, M. Andreeff, T. A. Donlon, M. L. Cleary, K. Suryanarayan, M. Homge, A. Redner, J. Gray and D. Pinkel, 1990. Detection of bcr-abl fusion in chronic myelogenous leukemia by in-situ hybridization. Science 250:559–562.
24. Meyne, J. and R. K. Moyzis, 1989. Human chromosome-specific repetitive DNA probes: Targeting in-situ hybridization to chromosome 17 with a 42-base-pair alphoid DNA oligomer. Genomics 4:472–478.
25. Kariya, Y., K. Kato, Y. Hayashizaki, S. Himeno, S. Tarui and K. Matsubara, 1987. Revision of consensus sequence of Alu repeats—a review. Gene 53:1–10.
26. Deininger, P. L. and C. W. Schmid, 1979. A study of the evolution of repeated DNA sequences in primates and the existence of a new class of repetitive sequences in primates. J. Mol. Biol. 127, 437–460.
27. Singer, M. F., 1982. Highly repeated sequences in mammalian genomes (review). Intl. Rev. Cytol. 76, 67–112.
28. Manuelidis, L., D. C. Ward, 1984. Chromosomal and nuclear distribution of the Hind III 1.9-kb human DNA repeat segment. Chromosoma 91:28–38.
29. Burke, T., G. F. Carle and M. V. Olson, 1987. Cloning of large segments of exogenous DNA into yeast by means of artificial chromosome vectors. Science 236:806–812.
30. Ludecke, H. J., G. Senger, U. Claussen and B. Horsthemke, 1989. Cloning defined regions of the human genome by microdissection of banded chromosomes and enzymatic amplification. Nature 338:348–350.

31. Denninger, P. L., D. J. Jolly, C. M. Rubin, T. Friedman and C. W. Schmid, 1981. Base sequence studies of 300 nucleotide renatured repeated human DNA clones. J.Mol.Bio. 151:17–33

32. Goldberg, M. L., R. P. Lifton, G. R. Stark and J. G. Williams, 1979. Isolation of specific RNAs using DNA covalently linked to diazobenzyloxymethyl cellulose or paper. Methods in Enzymology 68:206–220.

33. Noyes, B. E. and G. R. Stark, 1975. Nucleic acid hybridization using DNA covalently coupled to cellulose. Cell 5:301–310.

34. Brison, O., F. Ardeshir and G. Stark, 1982. General method for cloning amplified DNA by differential screening with genomic probes. Mol. Cell Biol. 2:578–587.

35. Hochgeschwender, U., J. G. Sutcliffe and M. B. Brennan, 1989. Construction and screening of a genomic library specific for mouse chromosome 16. PNAS 86:8482–8486.9.

36. Blin, N. and D. W. Stafford, 1976. A general method for isolation of high molecular weight DNA from eukaryotes. Nuc. Acid Res. 3:2303–2308.

37. van Ommen, G. J. B. and J. M. H. Verkerk, 1986. in "Human Genetic Diseases, A Practical Approach", ed. by K. E. Davies, 1986, IRL Press, Oxford, England.

38. Johnson, G. D. and J. G. M. de C. Noguieie Aroujo, 1981. A simple method of reducing the faking of immunofluorescence during microscopy. J. Immunol. Methods 43:349–350.

39. Thompson, L. H., L. L. Bachinski, R. L. Stallings, G. Dolf, C. A. Weber, A. Westerveld and M. J. Siciliano, 1989. Complementation of repair gene mutations on the hemizygous chromosome 9 in CHO: a third repair gene on human chromosome 19. Genomics 5:670–679.

40. Liu, P., D. F. Callen, S. T. Reeders, G. R. Sutherland, L. Thompson and M. J. Siciliano, 1989. Human DNA excision repair gene ERCC4 is located on chromosome 16 short arm 16p13.13-p13.3. Cytogenet. Cell Genet. 51:1035.

41. Liu, P., R. Legerski and M. J. Siciliano, 1989. Isolation of human transcribed sequences from human-rodent somatic cell hybrids. Science 246:813–815.

42. Stallings, R. L., E. Olson, A. W. Strauss, L. H. Thompson, L. L. Bachinski and M. J. Siciliano, 1988. Human creatine kinase genes on chromosomes 15 and 19, and proximity of the gene for muscle form to the genes for apolipoprotein C2 and excision repair. Am. J. Hum. Genet. 43:144–151.

43. Thompson, L. H., C. L. Mooney, K. Burkhart-Schultz, A. V. Carrano and M. J. Siciliano, 1985. Correction of a nucleotide-excision-repair mutation by human chromosome 19 in hamster-human hybrid cells. Somat. Cell Molec. Genet. 11:87–92.

44. Strife A., Clarkson B., "Biology of Chronic Myelogenous Leukemia," *Semin. Hematol,* 25:1 (1988).

45. Nowell P. C., Hungerford, D. A., "A Minute Chromosome in Human Chronic Granulocytic Leukemia, *Science,* 132:1497 (1960).

46. Rowley, J. D., "A New Consistent Chromosomal Abnormality in Chronic Myelogenous Leukemia Identified by Quinacrine Fluorescence and Giemsa Staining," *Nature,* 243:290 (1973).

47. Seong D. C., Liu P., Siciliano, J., Zhao, Y., Cork A., Henske, E., Warburton D., Champlin R., Trujillo J. M., Deisseroth A., and Siciliano, M. J., "Detection of Variant Ph'-Positive Chronic Myelogenous Leukemia Involving Chromosome #1, #9, and #22 by FISH Cancer Genetics and Cytogenetics," (in Press).

48. Tkachuk D. C., Westbrook, C. A., Andreeff M., Donlon T. A., Cleary, M. I. L., Suryanarayan K., Homge M., Redner A., Gray J., Pinkel D.: Detection of bcr-abl fusion in chronic myelogenous leukemia by in situ hybridization, *Science* 250:559 (1990).

49. Lengauer C., Riethman H. C., Speicher M. R., Taniwaki M., Konecki D., Green E. D., Becher R., Olson M. V., Cremer T.: "Metaphase and interphase cytogenetics with Alu-PCR-amplified yeast artificial chromosome clones containing the BCR gene and the protooncogenes c-raf-1, c-fms, and c-erbB-2¹, *Cancer Research,* 52:2590 (1992).

50. Henske E. P., Ozelius L., Anderson M. A., Kwiatkowski D. J.: "A radiation-reduced hybrid cell line containing 5 Mb/17 cM of human DNA from 9q34," *Genomics,* 13:841 (1992).

51. Trujillo J. M. , Cork A., Ahearn M. J., Youness E. L. , McCredie K. B.: Hematologic and cytologic characterization of 8/21 translocation in acute granulocytic leukemia, *Blood,* 53: 695 (1979).

52. Liu P., Siciliano J., Seong D., Craig J., Zhao Y., de Jong P. J., Siciliano M. J.: Dual Alu PCR primers and conditions for isolation of human chromosome painting probes from hybrid cells, *Cancer Genet. Cytogenet.* in press.

53. Kawasaki, E. S., Clark, S. S., Coyne, M. Y., Smith S. D., Champlin, R., Witte, O., McCormick, F. P., 1988. Diagnosis of chronic myelogenous and acute lymphocytic leukemias by detection of leukemia-specific mRNA sequences amplified in vitro. *Proc. Natl. Acad. Sci. USA,* 85:5698.

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i x ) SEQUENCE DESCRIPTION: SEQ ID NO:1:

GGATTACAGG YRTGAGCCA 19

( 2 ) INFORMATION FOR SEQ ID NO:2:

```
        ( i ) SEQUENCE CHARACTERISTICS:
                ( A ) LENGTH: 19 base pairs
                ( B ) TYPE: nucleic acids
                ( C ) STRANDEDNESS: single
                ( D ) TOPOLOGY: linear ( i x ) SEQUENCE DESCRIPTION: SEQ ID NO:2:
                    R C C A Y T G C A C   T C C A G C C T G                                   1 9

( 2 ) INFORMATION FOR SEQ ID NO:3:

( i ) SEQUENCE CHARACTERISTICS:
                ( A ) LENGTH: 31 base pairs
                ( B ) TYPE: nucleic acid
                ( C ) STRANDEDNESS: single
                ( D ) TOPOLOGY: linear ( i x ) SEQUENCE DESCRIPTION: SEQ ID NO:3:
                    G G C T G G G C G T   G G T G G C T C A Y   R C C T G T A A T C   C       3 1

( 2 ) INFORMATION FOR SEQ ID NO:4:

( i ) SEQUENCE CHARACTERISTICS:
                ( A ) LENGTH: 31 base pairs
                ( B ) TYPE: nucleic acids
                ( C ) STRANDEDNESS: single
                ( D ) TOPOLOGY: linear ( i x ) SEQUENCE DESCRIPTION: SEQ ID NO:4:
                    C C G A C C C G C A   C C A C C G A G T R   Y G G A C A T T A G   G       3 1

( 2 ) INFORMATION FOR SEQ ID NO:5:

( i ) SEQUENCE CHARACTERISTICS:
                ( A ) LENGTH: 19 base pairs
                ( B ) TYPE: nucleic acid
                ( C ) STRANDEDNESS: single
                ( D ) TOPOLOGY: linear ( i x ) SEQUENCE DESCRIPTION: SEQ ID NO:5:
                    Y G G T R A C G T G   A G G T C G G A C                                   1 9
```

What is claimed is:

1. A method for producing chromosome specific DNA probes comprising:

preparing a first and a second primer, each primer hybridizing to a region within a species specific repeat DNA segment wherein the first primer binds at or near the repeat segment 5' terminus and facilitates DNA replication in the direction of that terminus and the second primer binds at or near the same repeat segment at or near the repeat segment 3' terminus and facilitates DNA replication in the direction of that terminus;

simultaneously annealing both primers with a desired chromosome that has been obtained from species total chromosomal material; and amplifying the DNA from inter-repeat regions of the desired chromosome to produce DNA probe.

2. The method of claim 1 wherein each primer is part of a set of primers which hybridize at or near the repeat segment 3' or 5' terminus.

3. The method of claim 1 wherein the chromosome or segment thereof identified has species specific Alu segments.

4. The method of claim 1 wherein the first primer binds to a species specific repeat DNA consensus sequence located at or within 50 base pairs of the repeat sequence 5' terminus.

5. The method of claim 1 or claim 2 wherein primers comprising the first primer or primer set have a reverse complementary sequence to a consensus sequence located within a repeat segment.

6. The method of claim 1 wherein the repeat segment is a human Alu segment.

7. The method of claim 5 wherein the consensus sequence is located 13–31 base pairs from a human Alu 5' terminus.

8. The method of claim 2 wherein the second primer or primer set binds to a species specific repeat sequence located at or within 100 base pairs of the repeat sequence 3' terminus.

9. The method of claim 2 wherein the second primer or primer set binds with a human Alu consensus segment located from 240 to 258 base pairs from an Alu 3' terminus.

10. The method of claim 2 wherein primers comprising the second primer set have a sequence substantially identical to the human Alu repeat sequence located from base pair from 240 to 258.

11. The method of claim 2 wherein the first set of primers binds to a sequence located between base pairs 13 to 31 of a 5' end of a human Alu repeat consensus segment.

12. The method of claim 2 wherein the primers comprising the first set of primers differ in one or more base positions to facilitate binding to essentially all repeat sequences at base pairs 13–31 of human Alu repeat segments.

13. The method of claim 2 wherein the primers comprising the second set of primers differ in one or more base positions to facilitate binding to essentially all repeat sequences at base pairs 240–258 of human Alu repeat segments.

14. The method of claim 12 or claim 13 wherein the second set of primers comprises equal amounts of four primers.

15. A method for painting a human chromosome in metaphase spreads or interphase nuclei, comprising:

preparing DNA probe by the method of claim 1;

blocking or removing non-chromosome specific repeat sequences that may be present in the DNA probe;

labeling the DNA probe:

hybridizing the labeled DNA probe with a cell sample in which a selected human chromosome is to be detected; and detecting the human chromosome.

16. The method of claim 15 wherein the removing comprises the following steps:

obtaining a plasmid containing a complete human Alu repeat segment;

preparing a first plasmid arm primer from a known sequence of the plasmid arm adjacent to the 5' terminus of the Alu insert, wherein the primer will direct DNA synthesis toward an Alu-1 primer, said Alu-1 primer having a base sequence reverse complementary to a consensus sequence near the 5' end of the Alu repeat segment and directing DNA synthesis toward the plasmid arm primer;

preparing a second plasmid arm primer from a known sequence of the plasmid arm adjacent to the 3' terminus of the Alu insert, wherein the primer will direct the DNA synthesis toward an Alu-2 primer, said Alu-2 primer having a base sequence identical to a consensus sequence near the 3' end of the Alu repeat segment and directing DNA synthesis toward the plasmid arm primer;

polymerase chain reaction amplifying both Alu terminal regions located between each plasmid arm and the Alu consensus sequences binding to Alu-1 or Alu-2 primer;

adding human $C_0t$ 10 DNA;

linking the amplified Alu terminal regions and human $C_0t$ 10 DNA with the labeled probe; and separating carrier with bound non-chromosome specific repeat sequences from labeled probe.

17. The method of claim 16 wherein the plasmid is BLUR2 plasmid DNA.

18. A kit useful for preparing probes for inter-Alu-PCR specific for human chromosomes or segments of human chromosomes comprising a set of Alu-1 primers which have the base sequence GGATTACAGG YRTGAGCCA (seq id no:1) wherein Y is T or C and R is A or G and a second set of Alu-2 primers which have a base sequence RCCAYTGCAC TCCAGCCTG (seq id no:2) wherein Y is T or C and R is A or G.

19. A kit useful for the in-situ painting and banding of human chromosomes or segments of human chromosomes comprising detectably labeled DNA probes prepared in accordance with the method of claim 1.

20. The kit of claim 19 wherein the probes are specific for human chromosomes 1–22, the X and the Y chromosomes, chromosome segments 16p, 19 q13.3, 9q, 22q, 5q, 7q, 3p and 1q.

21. A nucleotide primer set comprising four primers having the following base sequence:

GGATTACAGG YRTGAGCCA (seq id no:1)

wherein Y is T or C and R is A or G and wherein the primers are characterized as binding near a 5' Alu terminus in a plurality of human Alu consensus segments or a nucleotide primer set comprising four primers having the following base sequence:

RCCAYTGCAC TCCAGCCTG (seq id no:2)

wherein Y is T or C and R is A or G and wherein the primers are characterized as binding near a 3' Alu terminus in a plurality of human Alu consensus segments.

22. An isolated DNA probe prepared by the method of claim 1 which hybridizes to a selected chromosome.

23. The DNA probes of claim 22 which are specific for human chromosomes 1–22, X chromosome, Y chromosome, 16p, 19q13.3, 9q, 22q, 5q, 7q, 3q and 1q.

24. An isolated DNA probe obtainable by the method of claim 1 wherein the desired chromosome specific segments amplified are from human chromosome segment 9q34.

25. An isolated DNA probe obtainable by the method of claim 1 wherein the desired chromosome specific probe is amplified from human chromosome segment 16p.

26. The isolated DNA probe of claim 23 wherein the 9q34 chromosome segment is about 5000 kb which is one-third distal and two-thirds proximal to the abl 1 locus.

27. A method of detecting Philadelphia positive chromosome cells comprising hybridizing genomic DNA from cells suspected of containing a rearranged bcr/abl gene with a detectably labeled probe that is in accordance with the probe of claim 26.

28. The method of claim 27 wherein the chromosome translocation is associated with chronic myelogenous leukemia (CML).

29. A method of detecting CML cells comprising:

hybridizing interphase cells suspected of containing a Philadelphia chromosome translocation with detectably labeled probe for bcr and abl gene wherein each probe is a chromosome specific DNA probe prepared by the method of claim 1 and wherein each probe is distinguishably detectable;

detecting the labeled bcr or abl gene segments;

simultaneously detecting the bcr and abl gene segments; and determining overlap of bcr and abl gene labels.

30. The kit of claim 19 wherein the DNA probe is in accordance with claim 26.

* * * * *